(12) United States Patent
Haarlander et al.

(10) Patent No.: US 10,039,933 B2
(45) Date of Patent: Aug. 7, 2018

(54) PHOTOTHERAPY DEVICE

(71) Applicants: Michael E. Haarlander, Vero Beach, FL (US); Thomas M. Haarlander, Vero Beach, FL (US)

(72) Inventors: Michael E. Haarlander, Vero Beach, FL (US); Thomas M. Haarlander, Vero Beach, FL (US)

( * ) Notice: Subject to any disclaimer, the term of this patent is extended or adjusted under 35 U.S.C. 154(b) by 0 days.

(21) Appl. No.: 14/248,486

(22) Filed: Apr. 9, 2014

(65) Prior Publication Data
US 2014/0303693 A1   Oct. 9, 2014

Related U.S. Application Data

(60) Provisional application No. 61/809,937, filed on Apr. 9, 2013, provisional application No. 61/835,744, filed on Jun. 17, 2013.

(51) Int. Cl.
A61N 5/06 (2006.01)
A61N 5/067 (2006.01)

(52) U.S. Cl.
CPC .......... *A61N 5/0616* (2013.01); *A61N 5/0624* (2013.01); *A61N 2005/067* (2013.01); *A61N 2005/0633* (2013.01); *A61N 2005/0645* (2013.01); *A61N 2005/0652* (2013.01)

(58) Field of Classification Search
CPC .... A61N 2005/0633; A61N 2005/0645; A61N 2005/0652; A61N 2005/067; A61N 2005/0655; A61N 5/06; A61N 5/0616; A61N 5/0624; A61F 5/451
USPC ...................................................... 607/88–91
See application file for complete search history.

(56) References Cited

U.S. PATENT DOCUMENTS

| | | | |
|---|---|---|---|
| 6,061,840 A | 5/2000 | Alligator | |
| 6,266,560 B1 * | 7/2001 | Zhang | A61N 1/36007 604/20 |
| 6,443,978 B1 * | 9/2002 | Zharov | 607/91 |
| 6,591,049 B2 | 7/2003 | Williams et al. | |
| 7,024,703 B1 * | 4/2006 | Della Ratta | A41B 9/023 2/400 |
| 7,101,384 B2 | 9/2006 | Benedict | |
| 7,261,730 B2 | 8/2007 | Friedman et al. | |
| 2005/0004631 A1 * | 1/2005 | Benedict | 607/88 |

(Continued)

FOREIGN PATENT DOCUMENTS

WO    WO 2013190579 A1 *  12/2013   ........... A61N 5/0616

OTHER PUBLICATIONS

International Preliminary Report on Patentability and Written Opinion of the International Searching Authority, PCT/US2014/033428 (Haarlander).

*Primary Examiner* — Nathan J Jenness
*Assistant Examiner* — Boniface N Nganga
(74) *Attorney, Agent, or Firm* — Wayne Edward Ramage; Baker Donelson

(57) ABSTRACT

A phototherapy device for applying light from a plurality of low-level light sources, such as LEDs or laser diodes, to male genitalia. The plurality of light sources are located on the interior of a tube, cup or helical band or ribbon, which is then applied to some or all portions of the male genitalia. One or more straps or arms may be used to position the device and hold it in place. A control unit may be wired or wirelessly connected to the device to power and control the frequency and timing of the light therapy application.

6 Claims, 44 Drawing Sheets

TOP

(56) References Cited

U.S. PATENT DOCUMENTS

| | | | |
|---|---|---|---|
| 2005/0197682 A1* | 9/2005 | Fox | A61N 5/0613 |
| | | | 607/88 |
| 2005/0234383 A1* | 10/2005 | Dougal | A61N 5/06 |
| | | | 604/5.02 |
| 2006/0001034 A1* | 1/2006 | Park | H01L 25/0753 |
| | | | 257/89 |
| 2008/0010716 A1* | 1/2008 | Brown et al. | 2/78.1 |
| 2009/0024063 A1* | 1/2009 | Kalvatanond | A61N 5/0613 |
| | | | 601/15 |
| 2009/0113605 A1* | 5/2009 | Nicolosi | A41B 9/023 |
| | | | 2/403 |
| 2009/0171260 A1* | 7/2009 | Lerma | 602/72 |
| 2009/0319008 A1* | 12/2009 | Mayer | A61N 5/0603 |
| | | | 607/90 |
| 2010/0094386 A1* | 4/2010 | Margolis et al. | 607/108 |
| 2011/0009794 A1* | 1/2011 | Diamond | A61F 5/40 |
| | | | 602/70 |
| 2013/0006335 A1* | 1/2013 | Lowe | 607/104 |
| 2013/0116612 A1* | 5/2013 | Stephan | A61N 5/06 |
| | | | 602/43 |
| 2013/0338742 A1* | 12/2013 | Gallen et al. | 607/108 |

\* cited by examiner

PHOTOTHERAPY DEVICE

This application claims benefit of and priority to U.S. Provisional Application No. 61/809,937, filed Apr. 9, 2013, by Michael E. Haarlander, et al., and U.S. Provisional Application No. 61/835,744, filed Jun. 17, 2013, and is entitled to that filing date for priority. The specification, figures and complete disclosures of U.S. Provisional Application Nos. 61/809,937 and 61/835,744 are incorporated herein by specific reference for all purposes.

FIELD OF INVENTION

This invention relates to a device and related method for phototherapy or light therapy applications to male genitalia.

BACKGROUND OF INVENTION

Physicists have recognized light to be a pure form of energy that is a part of the electromagnetic radiation spectrum. Within this spectrum, the various colors of light each represent unique wavelengths and frequencies that produce therapeutic effects when absorbed through the skin of the body. Near infrared wavelengths are longer than visible light wavelengths, and have been found to penetrate to a deeper level of muscle, bones and joints. Visible red light tends to stimulate growth at the cellular level whereas blue light has more of a soothing affect.

Further scientific research has found that the application of low-level light therapy on the body produces a photochemical reaction in the cell. During this process, a photon of light is absorbed into the treated cell to increase and stimulate stored energy. As a result, this stored energy can be used to perform various cellular tasks and produce increased levels of ATP, NADH, protein, RNA, and nitric oxide.

The effect of light on nitric oxide and the cardiovascular system is well known. Red blood cells and endothelial cells absorb light wavelengths directly through the skin, which release nitric oxide into the smooth muscle cells lining small blood vessels. In the cell, the nitric oxide binds to the enzyme, guanylate cyclase, and increases levels of cyclic guanosine monophosphate, causing the smooth muscle cell to relax. This leads to vasodilation.

This vasodilation effect can result from both natural and artificial light. Studies have shown that red and near infrared light enhance the release of nitric oxide, and thus vasodilation. Infrared wavelengths are longer than visible light wavelengths, and have been found to penetrate to a deeper level of muscle, bones and joints.

Low level light therapy enhances blood flow, as documented in the following reports, which are incorporated herein by specific reference for all purposes (the abstracts are attached as an appendix to U.S. Provisional Application No. 61/809,937, to which this application claims priority):

Zaidi, et al., "Transient Repetitive Exposure to Low Level Light Therapy Enhances Collateral Blood Vessel Growth in the Ischemic Hindlimb of the Tight Skin Mouse," Photochem. Photobiol., Dec. 11, 2012.

Okuni, I., "Phototherapy in Rehabilitation Medicine," Masui., July 2012.

Saied, et al., "The diabetic foot and leg: combined He—Ne and infrared low-intensity lasers improve skin blood perfusion and prevent potential complications. A prospective study on 30 Egyptian patients," Lasers Med. Sci., September 2011.

Plass, et al., "Light-induced vasodilation of coronary arteries and its possible clinical implication," Ann. Thorac. Surg., April 2012.

Shurygina, et al., "Effect of infrared low-intensity laser therapy on orbital blood circulation in children with progressive short sightedness," Vopr Kurortol Fizioter Lech Fiz Kult., September-October 2009.

SUMMARY OF INVENTION

In various embodiments, the present invention comprises a plurality of devices and related methods for phototherapy or light therapy treatment applications to male genitalia. The devices and methods described below apply low-level light of different frequencies to male genitalia, and can be used to address erectile dysfunction, herpes, prostate issues, gonorrhea, chlamydia, syphilis, human papilloma virus, genital warts, chancroids, ectoparasitic infections, and other type of skin conditions in the genital region.

In general, the devices of the present invention use a plurality of semiconductor light sources, such as, but not limited to, light-emitting diodes (LEDs), laser diodes, fiber optics, full spectrum light sources, or a combination thereof, that provide therapeutic and rejuvenating effects to human tissue through close proximity to the skin or body part. In particular, the devices provide the therapeutic effects of enhancing blood flow and the repair of tissue damage, the deletion of cellular memory, and general rejuvenation and wellness. The light sources emit energy in the form of photons when switched on, which delivers energy to targeted tissue, penetrating the layers of skin to produce a non-thermal photochemical effect at the cellular level. The therapy is noninvasive, and avoids the potential side effects of other forms of therapy, such as drug therapy. The light therapy may be combined vibrational therapies such as sonic or ultrasonic.

In several embodiments, the light sources are in full contact with the tissue. The light penetrates the layers of skin to reach internal tissues to provide a specific, non-thermal photochemical effect at the cellular level. Low-level light therapy using the devices herein offer a safe and effective approach without undue side-effects by providing a more immediate, direct, and safer mode of application than previously known in the art. The light sources are placed in direct contact with the skin, perpendicularly or as close to being perpendicular as reasonably possible.

In one embodiment, the device comprises a tube with an open cup affixed to one end of the tube. The tube is open on the end affixed to the cup, and may or may not be open on the other end. A plurality of light sources, such as LEDs or laser diodes, are placed on the inside of the tube and also may be placed on the top side of the cup. Holes may be placed in the device to allow air-flow. The shaft of the male phallus is placed into the tube, and the cup is adapted to hold the testicles. One or more straps or arms may be used to help position the device and hold it in place. In the embodiment shown, a control unit is connected by a cord and plug with the device to power and control the frequency and timing of the light therapy application.

In another embodiment, the tube is replaced by a helical or spiral band or ribbon, with light sources on the interior, which can be wrapped around the shaft of the male genitalia. The band or ribbon can be freestanding, or attached to the cup, or to one of the straps or arms.

In yet another embodiment, the device comprises a single cup, into which the entire male genitalia is placed. While this embodiment may not provide as thorough contact with the skin, it may be more comfortable or easier to use for some individuals.

It should be noted that the device may be made of any suitable material, such as plastic, metal, steel, rubber, fabric, or any combination thereof, and may be rigid or flexible in whole or in part. The device may be made in a variety of colors, sizes and configurations. The device may be lined on the interior, such as with a soft foam or the like. There may be various configurations or patterns of light sources, in a variety of colors and intensities (i.e., milliwatt range). Different colors may be used for different treatments.

The device may simply be worn underneath underwear, or in a specially-designed support garment, such as a jockstrap, shorts, or belt.

The light sources can be controlled by wireless or wired connection with a computing device operating a control program, a touchpad monitor or device on or connected to the cast, or a control unit or box. The user can control color, type, duration, wavelength amplitude, wavelength phase, and frequency (pulse) of the light sources being activated during therapeutic application, as described in further detail below.

Power for the invention may be provided by plugging the device into a standard electrical outlet. Alternatively, one or more batteries may be provided.

The device may be made in a variety of colors, sizes and configurations. There may be various configurations or patterns of LEDs or laser diodes, in a variety of colors and intensities (i.e., milliwatt range). Different colors may be used for different treatments.

In one embodiment, RGB technology utilizes the color mixing properties of red, green, and blue LED chips that are provided on a reflector. A photomixing material and filler resin scatters the light rays to uniformly combine the rays emitted from the LED chips. The photomixing material and filler resin are applied onto upper sides of the light emitting diode chips while being mixed with each other, and the photomixing material is uniformly dispersed in the filler resin.

In several embodiments, the light sources include red, blue, green and orange colors. In one embodiment, the invention can run any light frequency within the pulsing range of 0 Hz to 100,000,000,000 Hz, and can run all safe wavelengths of the electromagnetic spectrum, including visible light and near-infrared light. In one exemplary embodiment, the power output per laser diode, LED, or fiber optic ranges from 1 mW to 300 mW.

In another exemplary embodiment, the invention produces specific wavelengths in the form of linear waves, including, but not limited to, sine, square, triangular, and saw tooth waves. Additional wave types can be produced, including, but not limited to, solution waves, a self-reinforcing solitary wave (a wave packet or pulse) that maintains its shape while it travels at constant speed, and longitudinal waves capable of passing through tissue from one side to another with no loss of strength. The utilization of a single wave type or combination of wave types produces a wavelength with no degradation to wave shape allowing the energy produced from the wave to penetrate any desired depth of biological tissue.

In a further embodiment, the present invention incorporates the geometric configuration of single light technology or multiple light technologies, wavelength, amplitude and power output, referred to as the array. The geometric configuration is not limited to any single configuration and can include any geometric configuration of wavelengths, power output, amplitude, and wave types. The array is engineered to produce multiple wavelengths, power outputs, amplitudes and wave types producing therapeutic benefits to biological tissue. This is accomplished by utilizing expandable software, smart chips, adaptive lenses, and light producing technology that is completely scalable and configurable to operator needs. The geometric arrangement of the light technology is not limited to any single geometric configuration, wavelength, power output, amplitude, or wave type. The array can be configured to support any geometric configuration of multiple wavelengths, multiple power outputs, multiple amplitudes, or multiple wave types.

Using the applicable control mechanism, in one embodiment the operator or user can control the frequency, amplitude, and phase of the wavelengths through a digital interface. The operator can select the frequency (pulse), wavelength, amplitude, and wave type associated with each light-emitting source. This phase relationship allows for each channel to be specifically programmed with frequency and peak-to-peak amplitude allowing multiple channels to operate at a different frequency (pulse) and amplitude. Thus, the phototherapy device can produce multiple wavelengths, multiple wave types, multiple frequencies (pulses), and multiple amplitudes. It also can be used to provide and control vibrational therapies, including but not limited to sonic or ultrasonic or combinations thereof.

In one particular embodiment, the present invention will only work with specific control boxes, accessories, or computing devices, which can be self-identifying through "handshake" communications technology. Utilizing handshake technology will only pair specific units to specific accessories. A specific circuit board chip may be utilized in each and every piece of equipment. These chips include a one-of-a-kind code that forms a unique link to each other. The circuit board may be a variable frequency circuit board. Specific RF chips may be installed in each and every unit so that identifications can be placed into each piece of equipment to identify purchase dates and other necessary information.

In yet a further embodiment, the invention is equipped with an USB port and wireless circuit board that will operate and control peripheral devices by the digital interface of the phototherapy device. Peripheral devices are not limited to and include light technology devices and any device that generates frequency or electrical pulse. The peripheral devices will be activated upon a passcode entered into the digital interface of the phototherapy device.

DETAILED DESCRIPTION OF EXEMPLARY EMBODIMENTS

In various embodiments, the present invention comprises a plurality of devices and related methods for phototherapy or light therapy treatment applications to male genitalia. The devices and methods described below apply low-level light of different frequencies to male genitalia, and can be used to address erectile dysfunction, herpes, prostate issues, gonorrhea, chlamydia, syphilis, human papilloma virus, genital warts, chancroids, ectoparasitic infections, and other type of skin conditions in the genital region.

In general, the devices of the present invention use a plurality of semiconductor light sources 6, such as, but not limited to, light-emitting diodes (LEDs), laser diodes, fiber optics, full spectrum light sources, or a combination thereof, that provide therapeutic and rejuvenating effects to human tissue through close proximity to the skin or body part. In particular, the devices provide the therapeutic effects of enhancing blood flow and the repair of tissue damage, the deletion of cellular memory, and general rejuvenation and wellness. The light sources emit energy in the form of photons when switched on, which delivers energy to targeted tissue, penetrating the layers of skin to produce a non-thermal photochemical effect at the cellular level. The therapy is noninvasive, and avoids the potential side effects of other forms of therapy, such as drug therapy. The light therapy may be combined vibrational therapies such as sonic or ultrasonic.

In several embodiments, the light sources are in full contact with the tissue. The light penetrates the layers of skin to reach internal tissues to provide a specific, non-thermal photochemical effect at the cellular level. Low-level light therapy using the devices herein offer a safe and effective approach without undue side-effects by providing a more immediate, direct, and safer mode of application than previously known in the art. The light sources are placed in direct contact with the skin, perpendicularly or as close to being perpendicular as reasonably possible.

Figure 1:
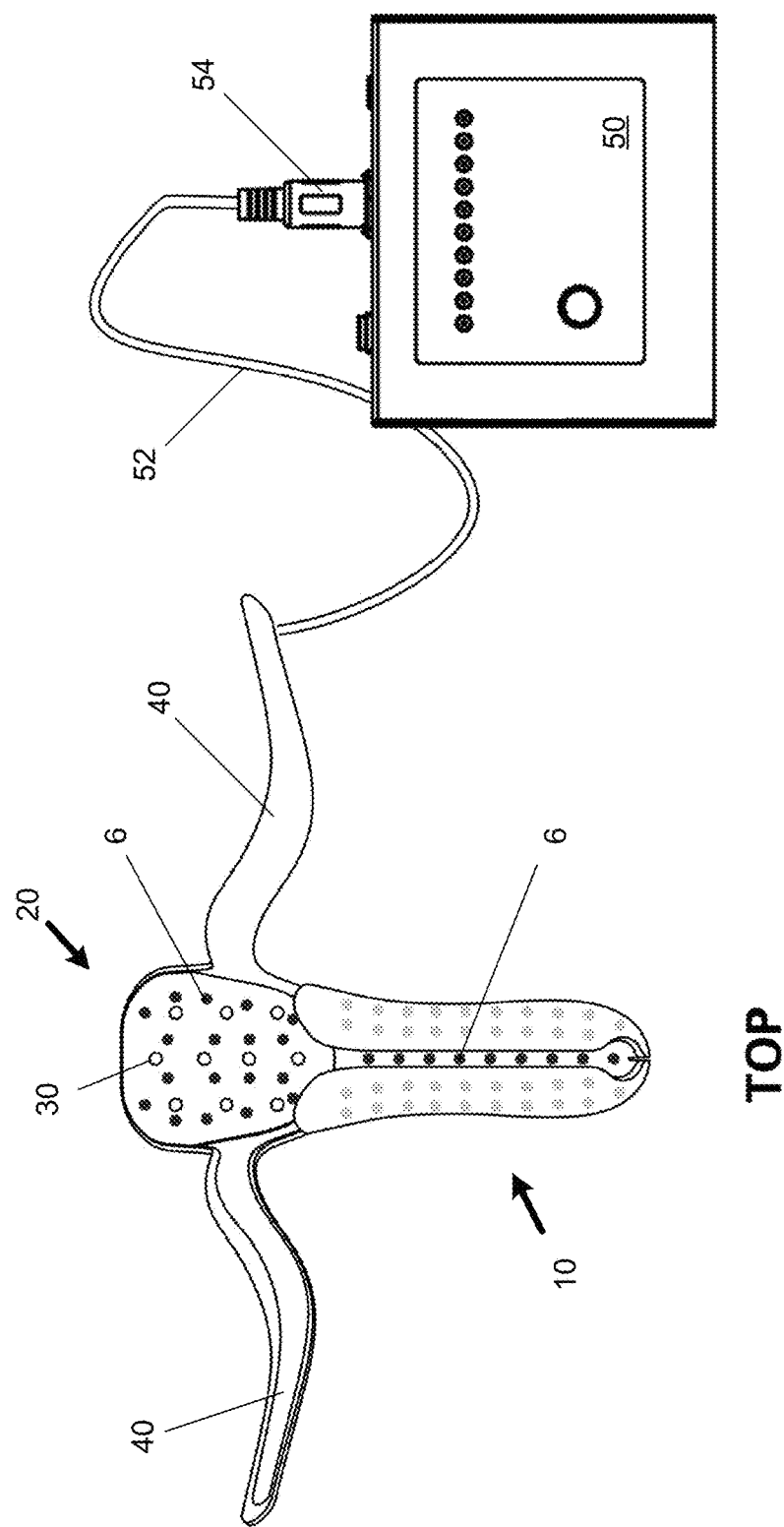
FIG. 1 shows a front view of a phototherapy device with tube and cup connected to a control box, in accordance with an embodiment of the present invention.
Figure 2:
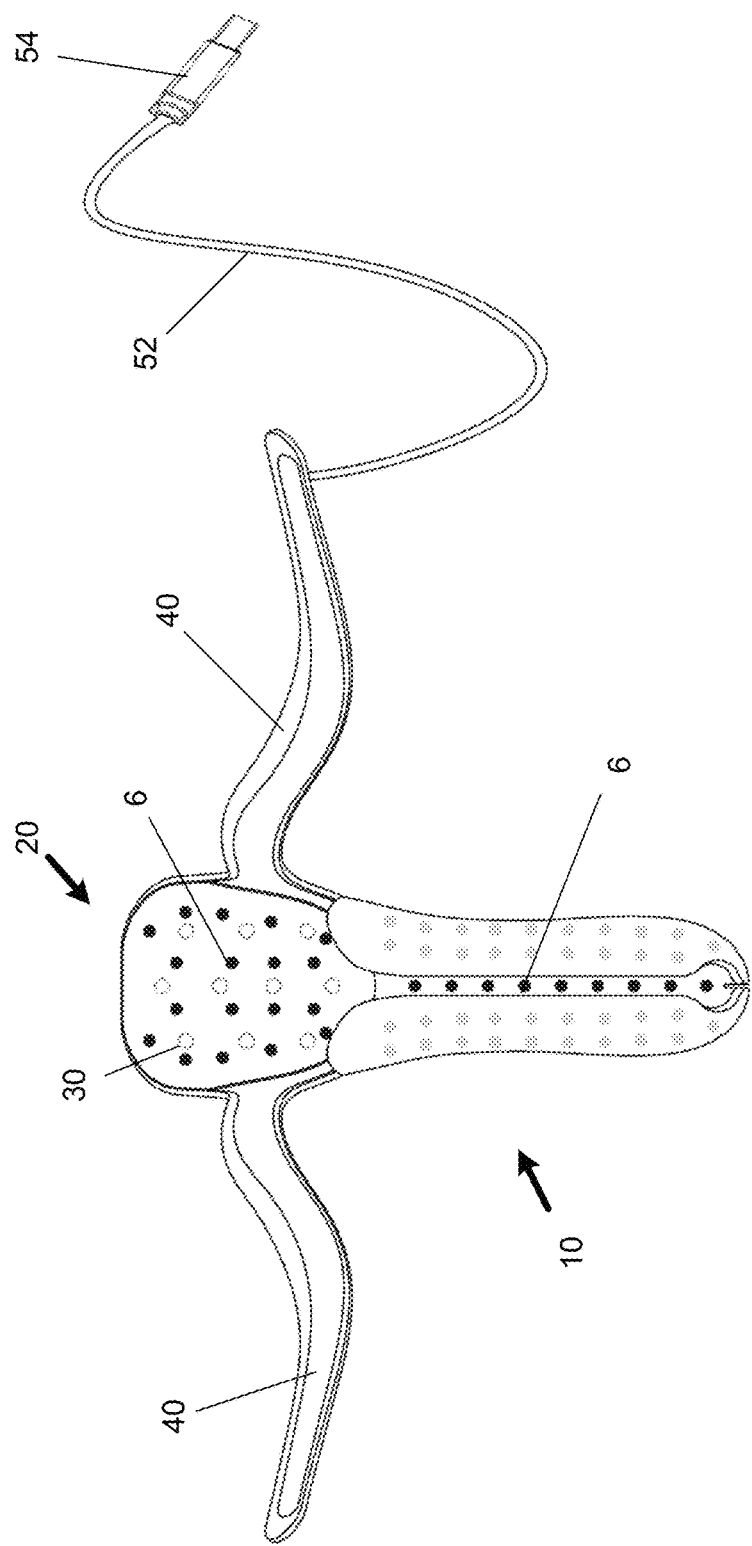
FIG. 2 is another front view of the device of FIG. 1.
Figure 3:
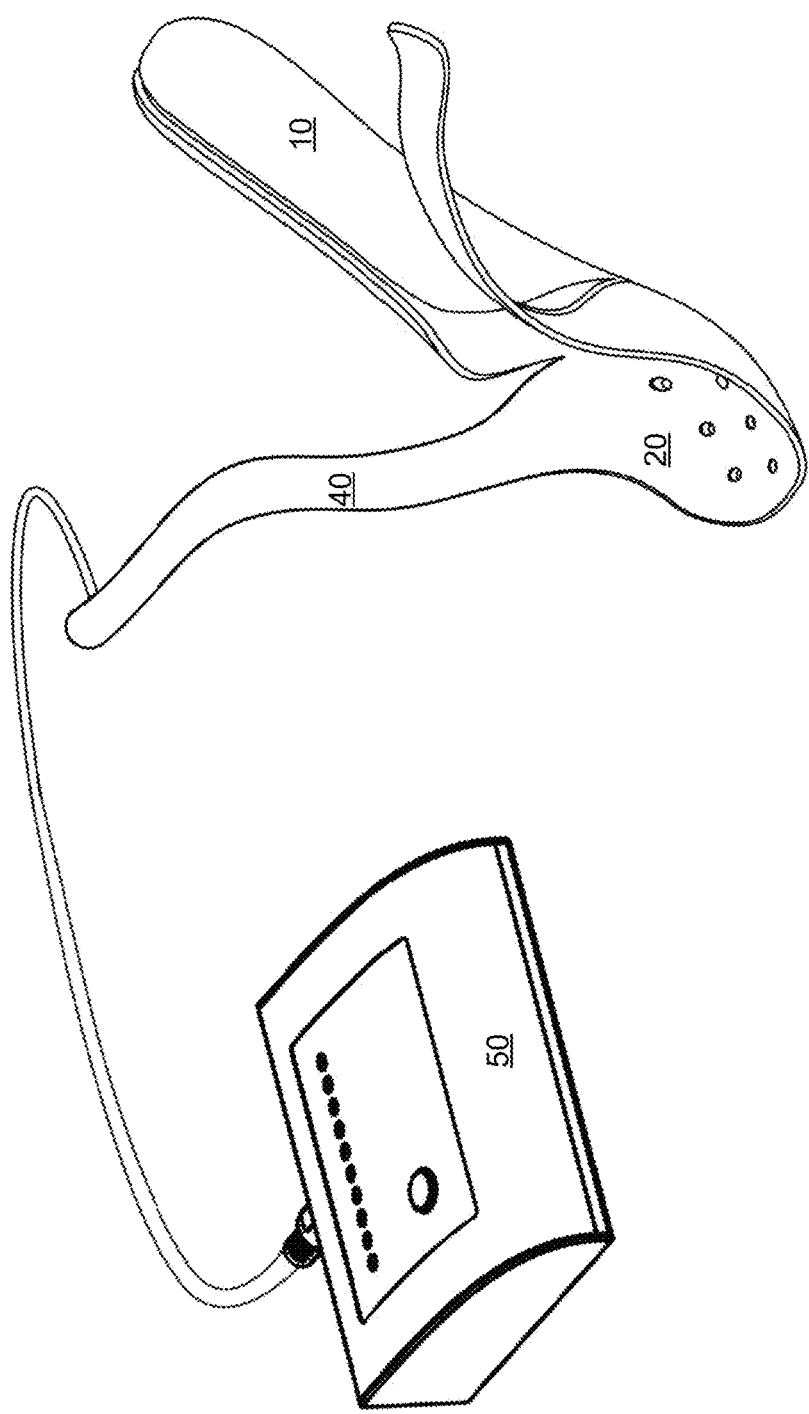
FIG. 3 is a perspective view of the device of FIG. 1.
Figure 4:
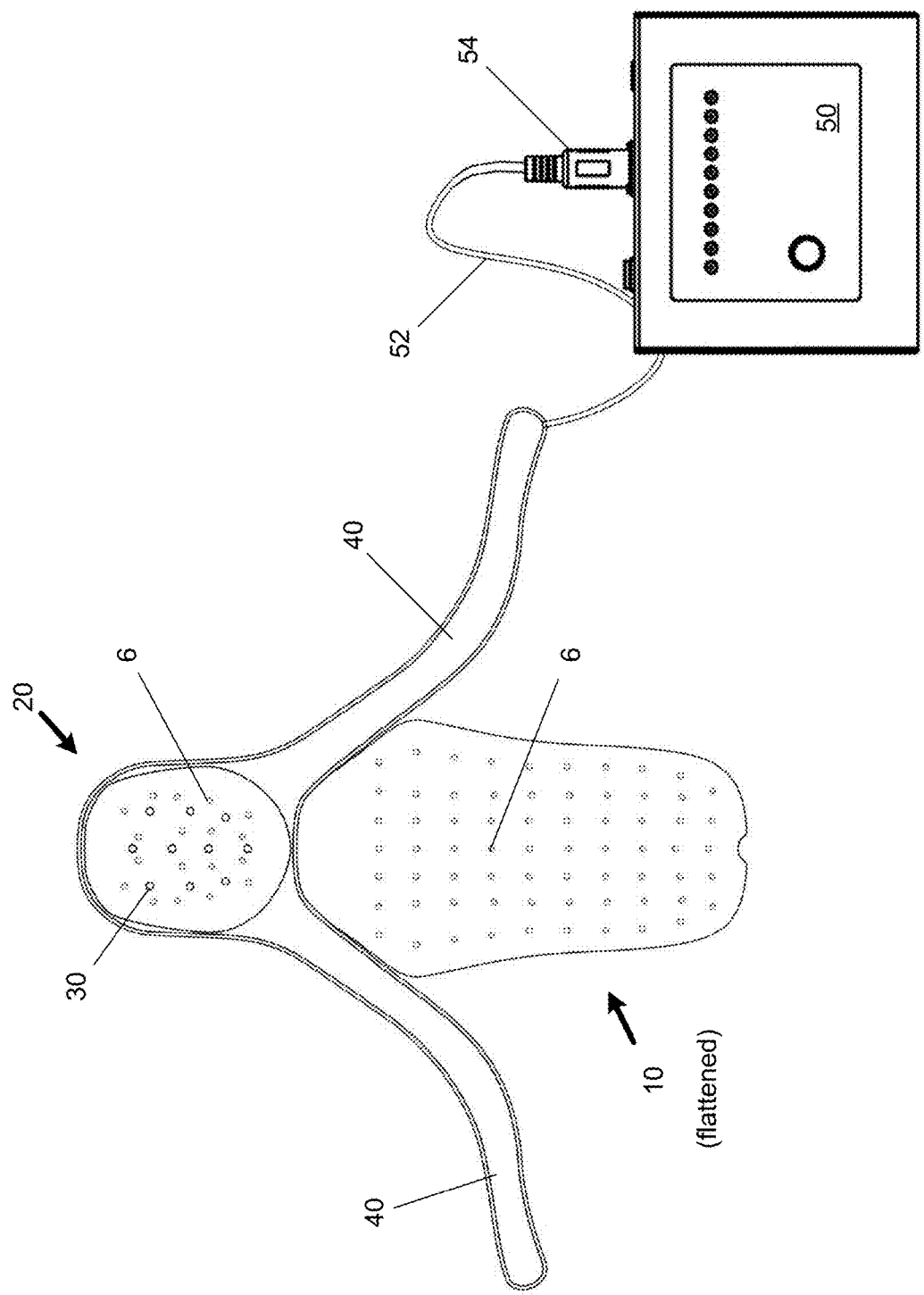
FIG. 4 is a top view of the device of FIG. 1, with control box.
Figure 5:
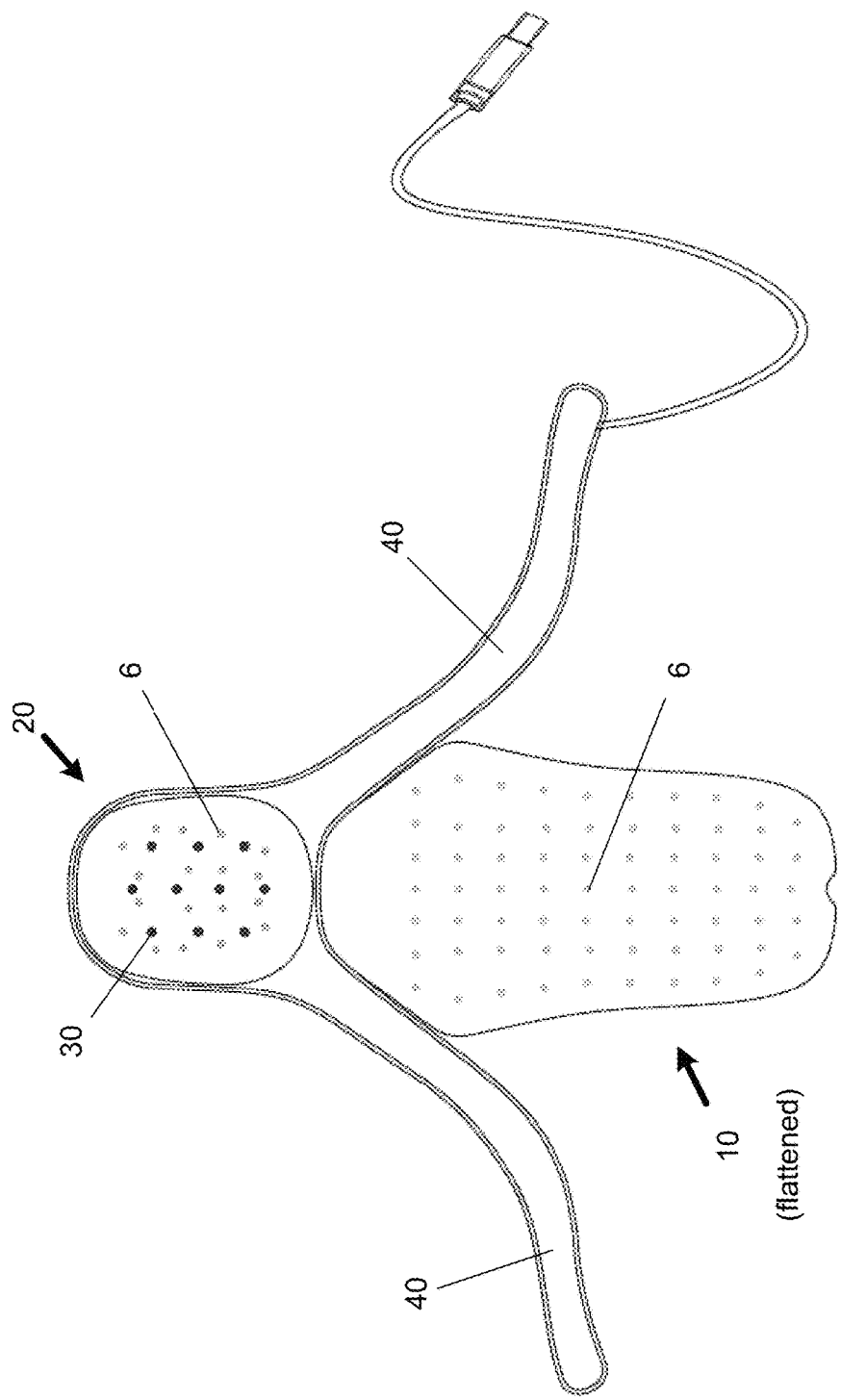
FIG. 5 is another top view of the device of FIG. 1.
Figure 6:
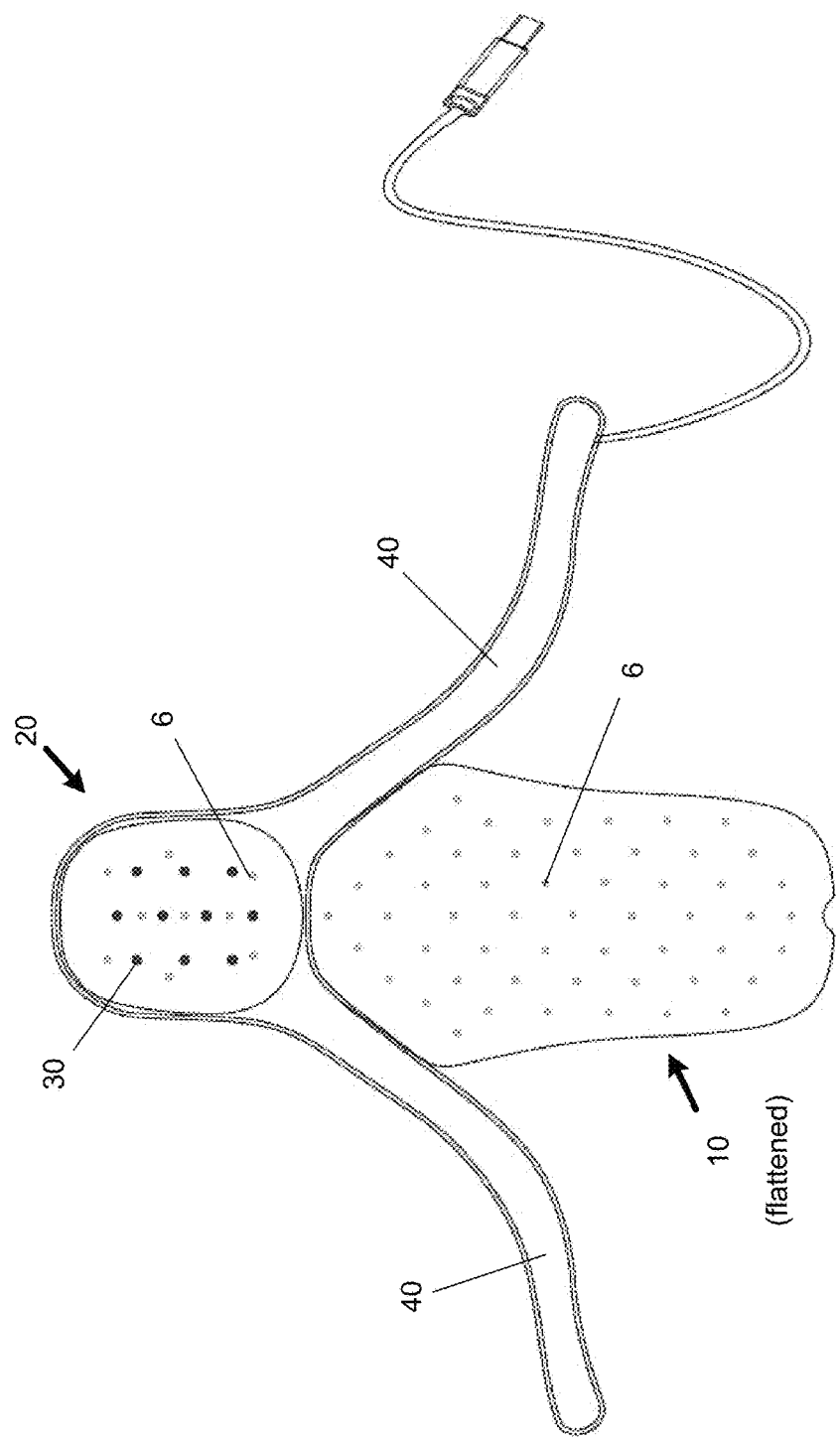
FIG. 6 is another top view of the device of FIG. 1, with an alternative light source pattern.
Figure 7:
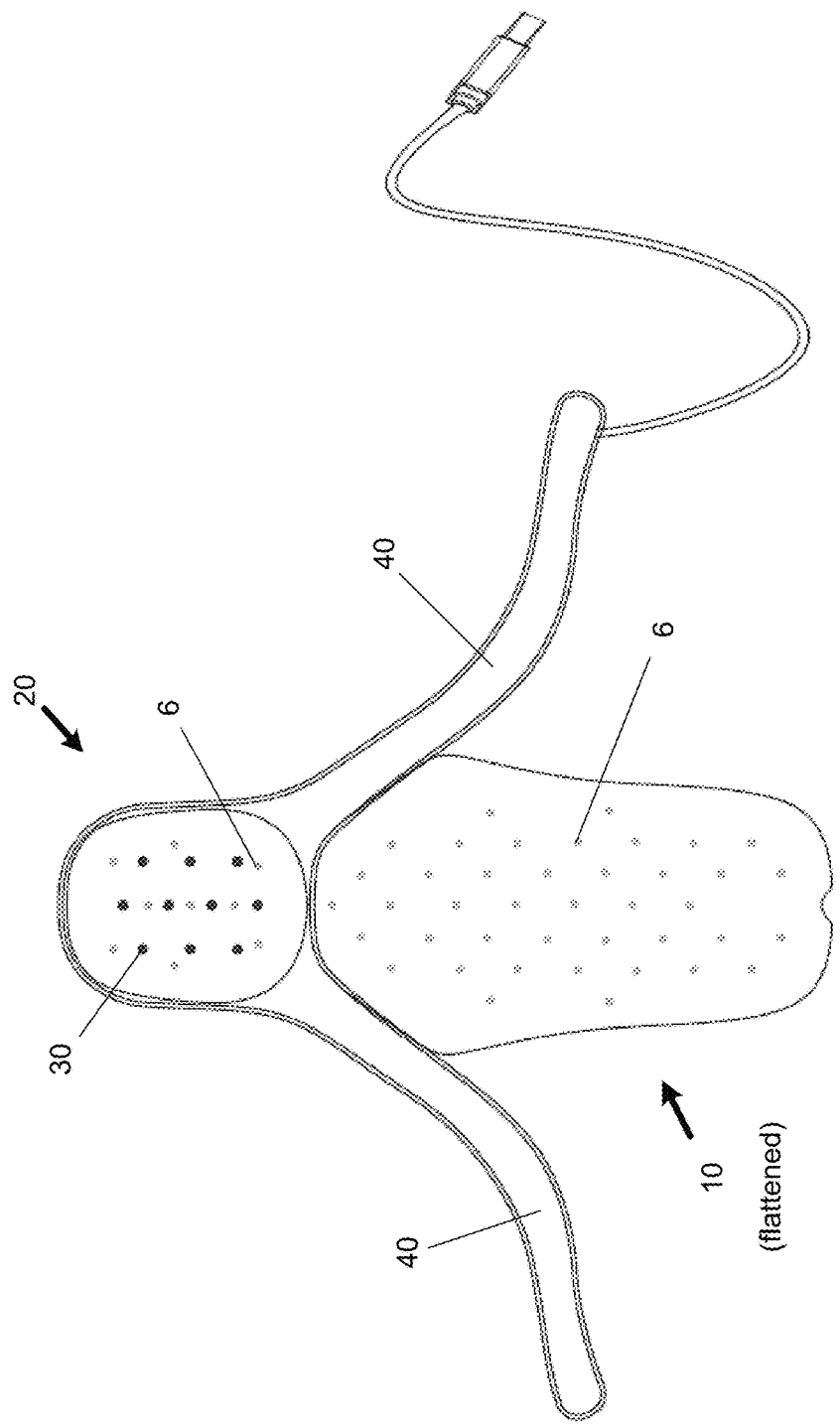
FIG. 7 is another top view of the device of FIG. 1, with an alternative light source pattern.

In one embodiment, as shown in FIGS. 1-7, the device comprises a tube 10 with an open cup 20 affixed to one end of the tube. The tube is open on the end affixed to the cup, and may or may not be open on the other end. A plurality of light sources 6, such as LEDs or laser diodes, are placed on the inside of the tube and also may be placed on the top side of the cup. Holes 30 may be placed in the device to allow air-flow. The shaft of the male phallus is placed into the tube, and the cup is adapted to hold the testicles. One or more straps or arms 40 may be used to help position the device and hold it in place. In the embodiment shown, a control unit 50 is connected by a cord 52 and plug 54 with the device to power and control the frequency and timing of the light therapy application.

Figure 8:
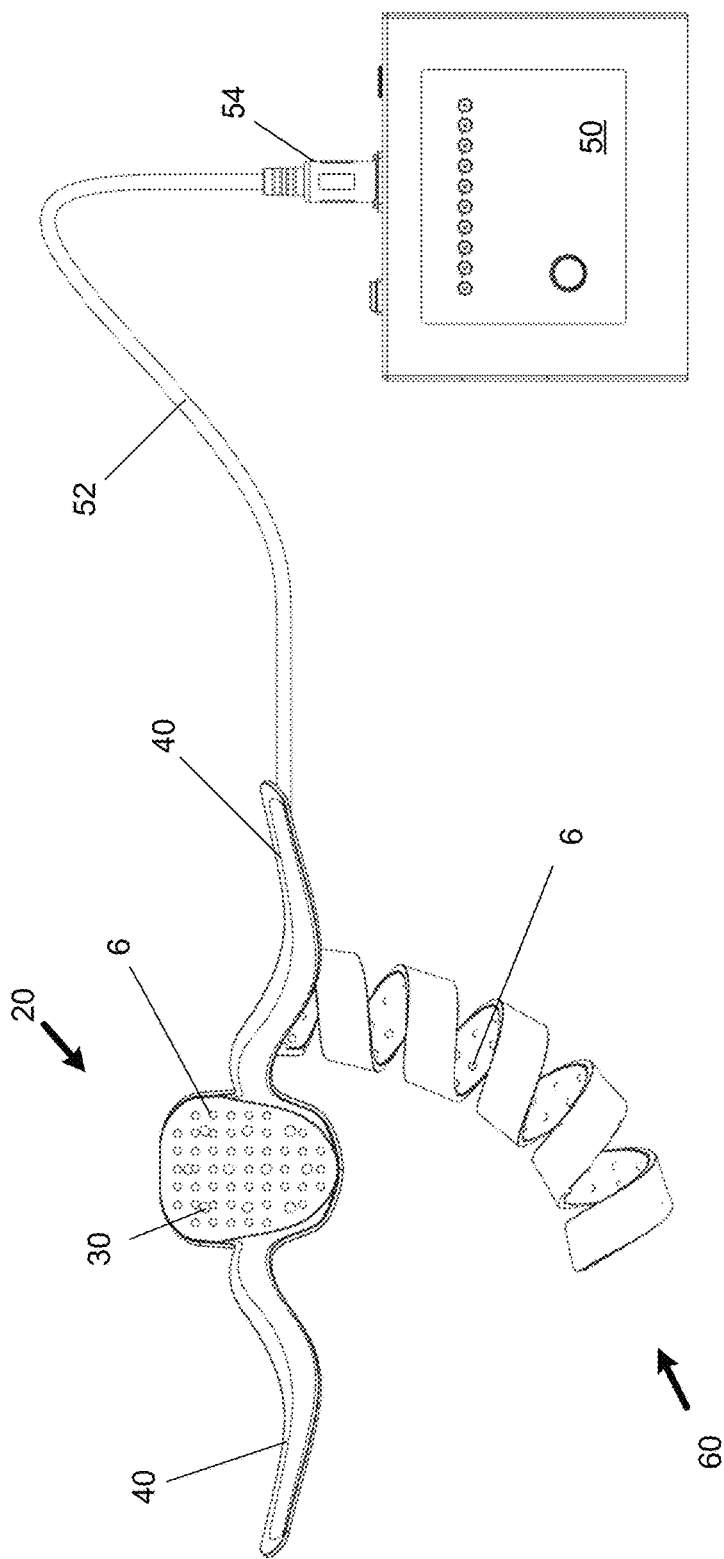
FIG. 8 shows a top view of another phototherapy device with helical tube or strip and cup connected to a control box, in accordance with an embodiment of the present invention.
Figure 9:
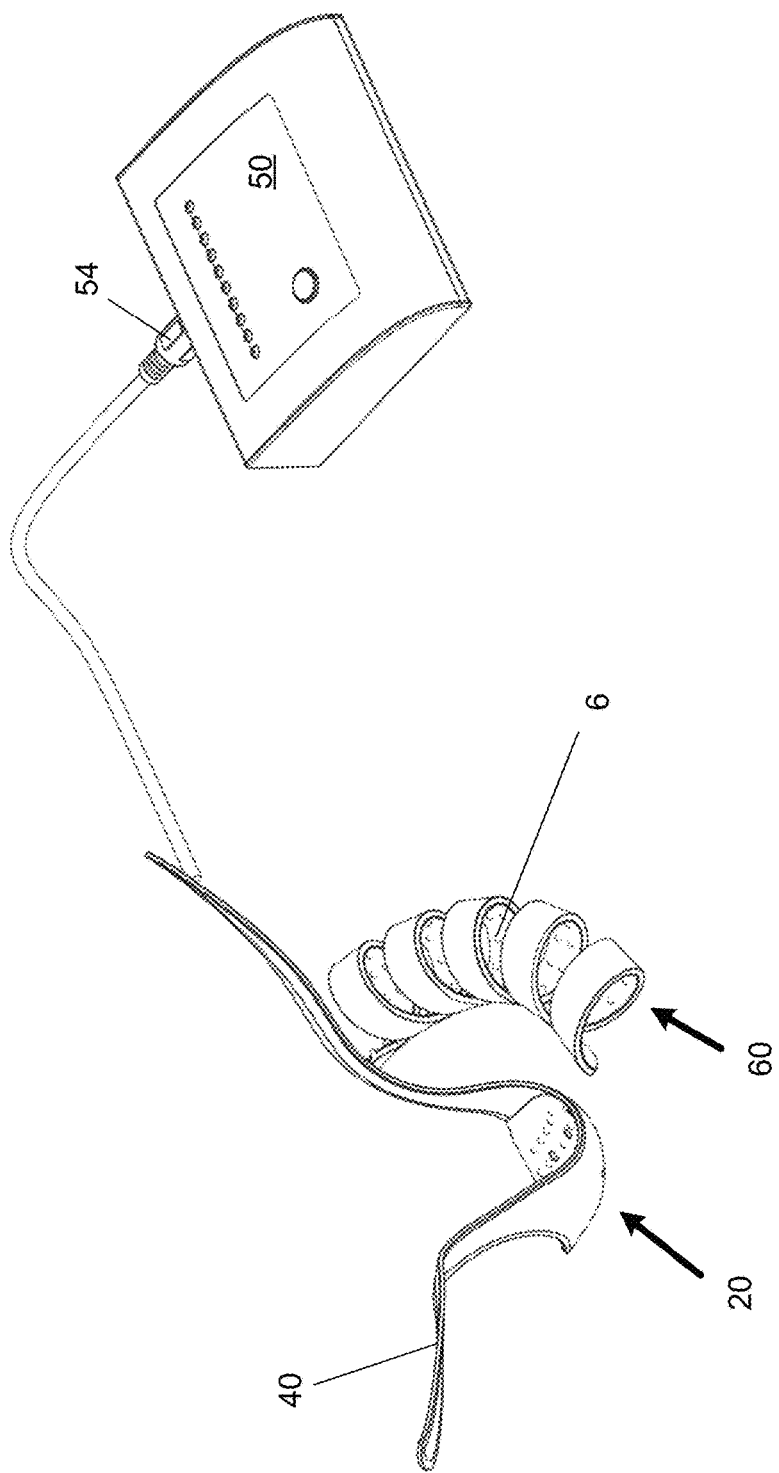
FIG. 9 shows a perspective view of the device of FIG. 8.
Figure 10:
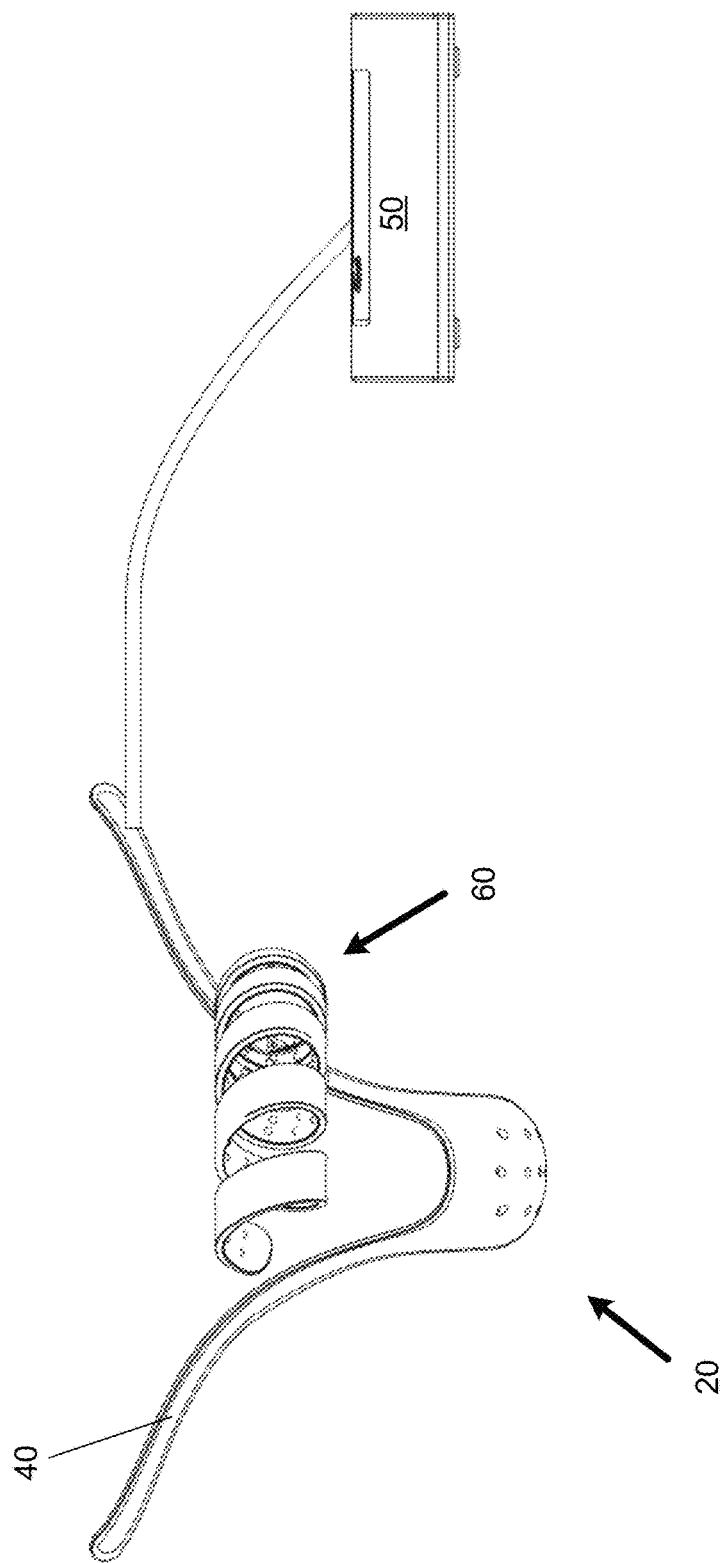
FIG. 10 shows a front view of the device of FIG. 8.
Figure 11:
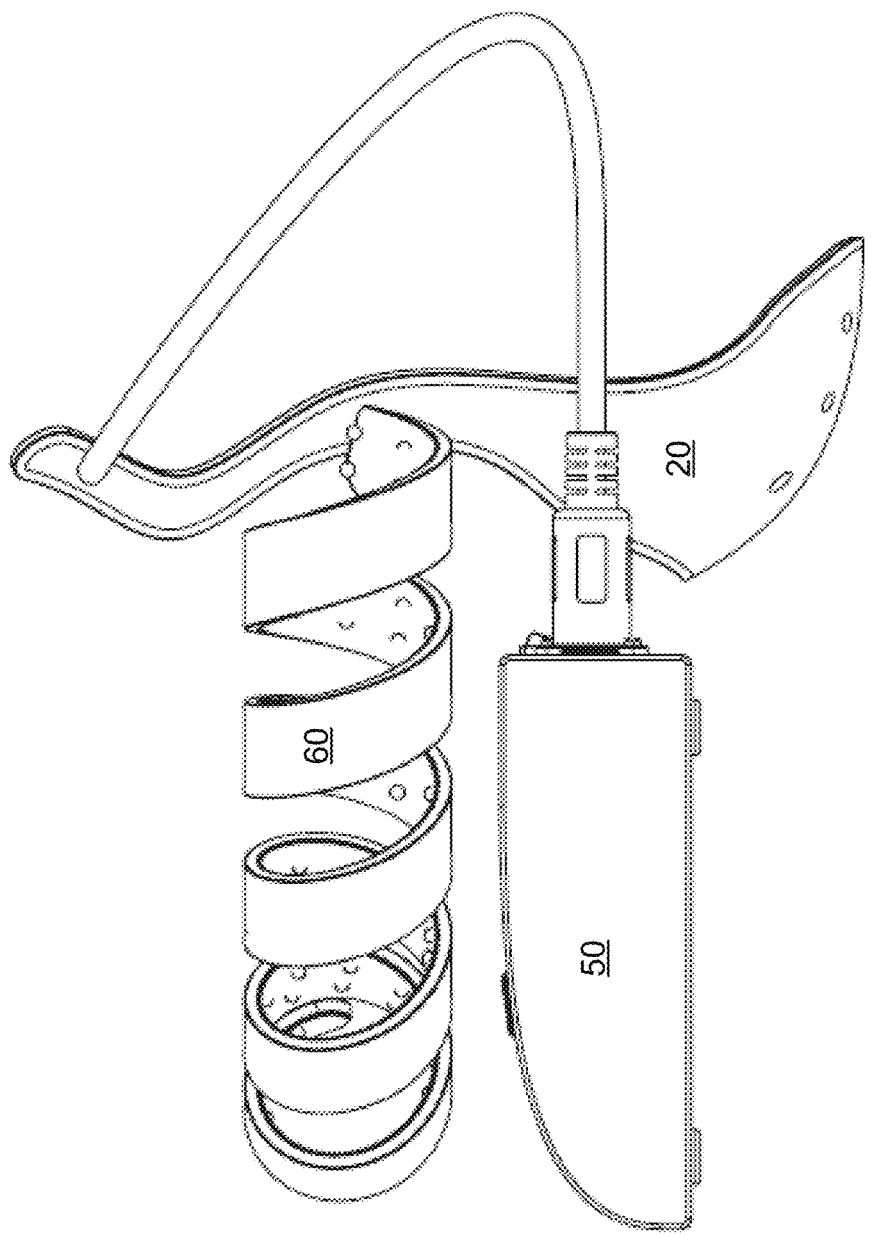
FIG. 11 shows a left side view of the device of FIG. 8.
Figure 12:
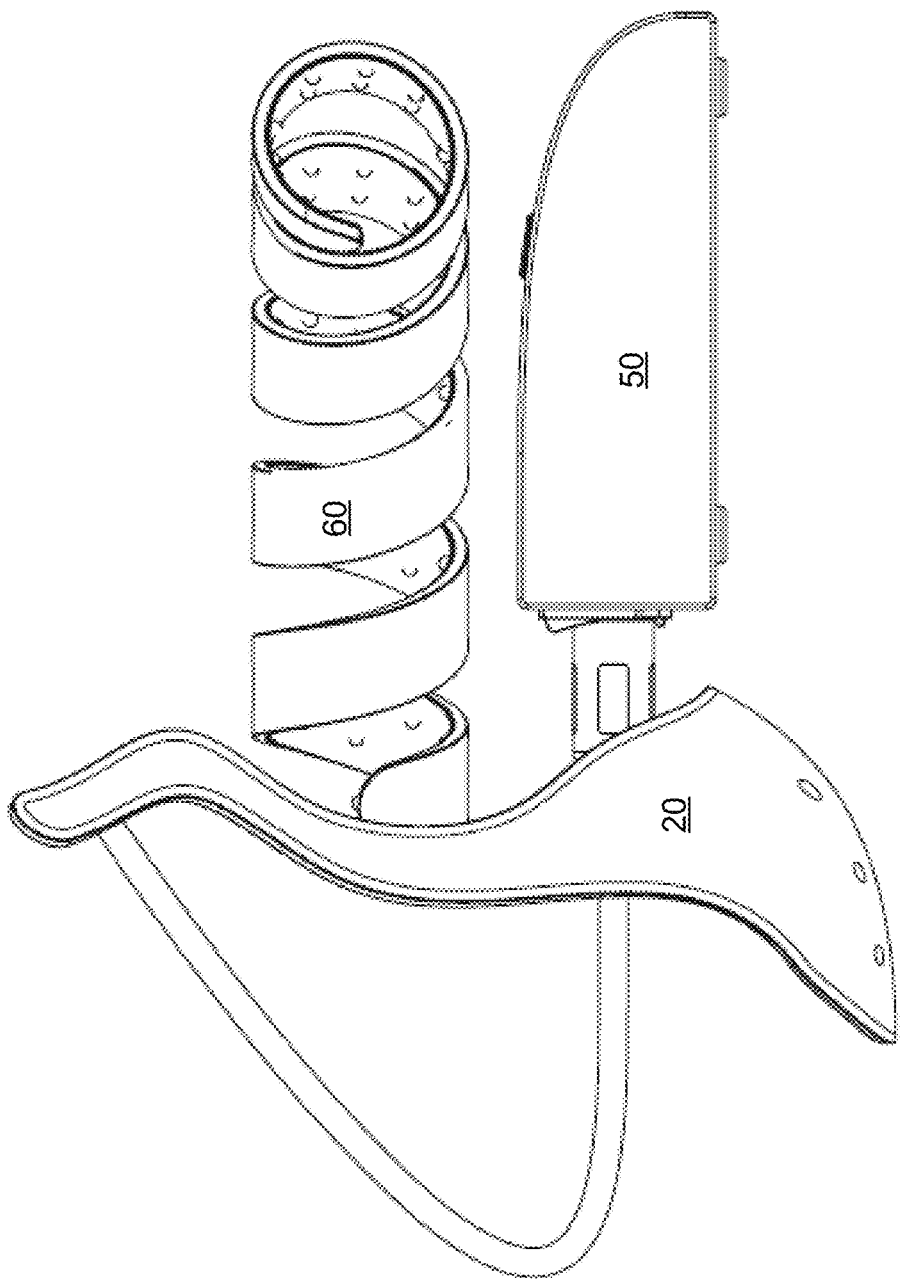
FIG. 12 shows a right side view of the device of FIG. 8.
Figure 13:
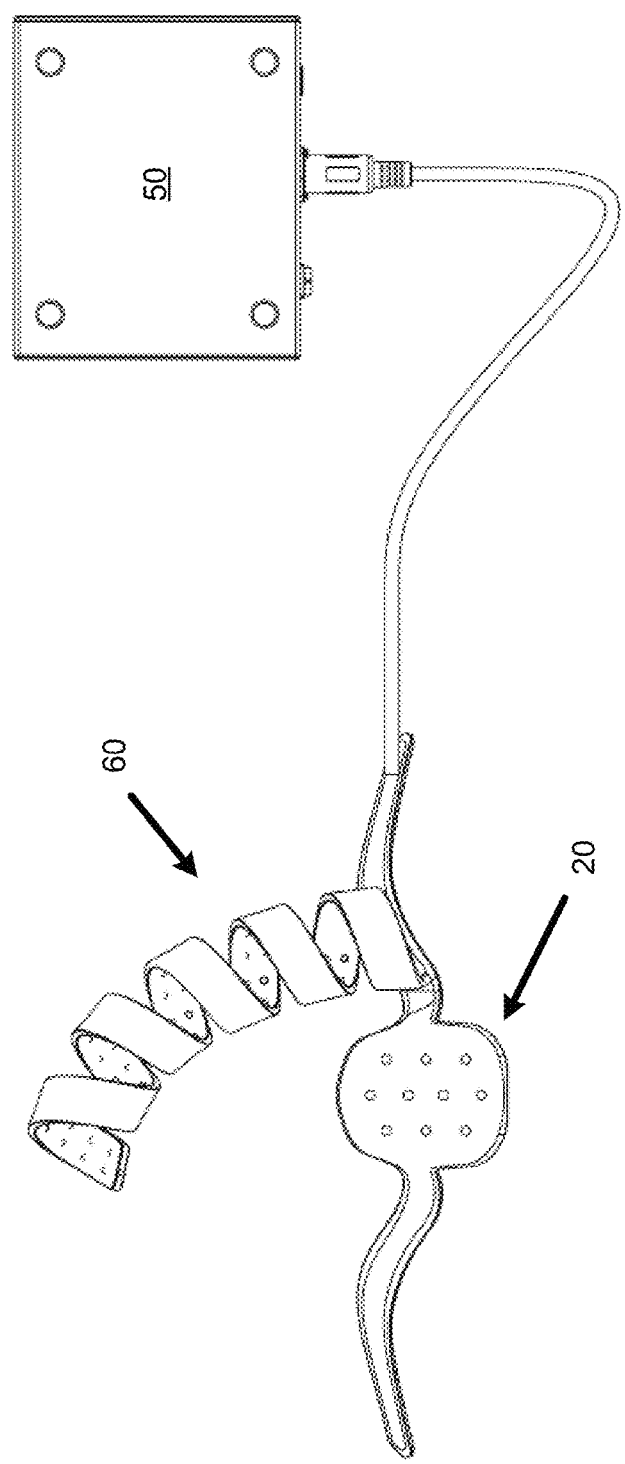
FIG. 13 shows a bottom view of the device of FIG. 8.
Figure 14:
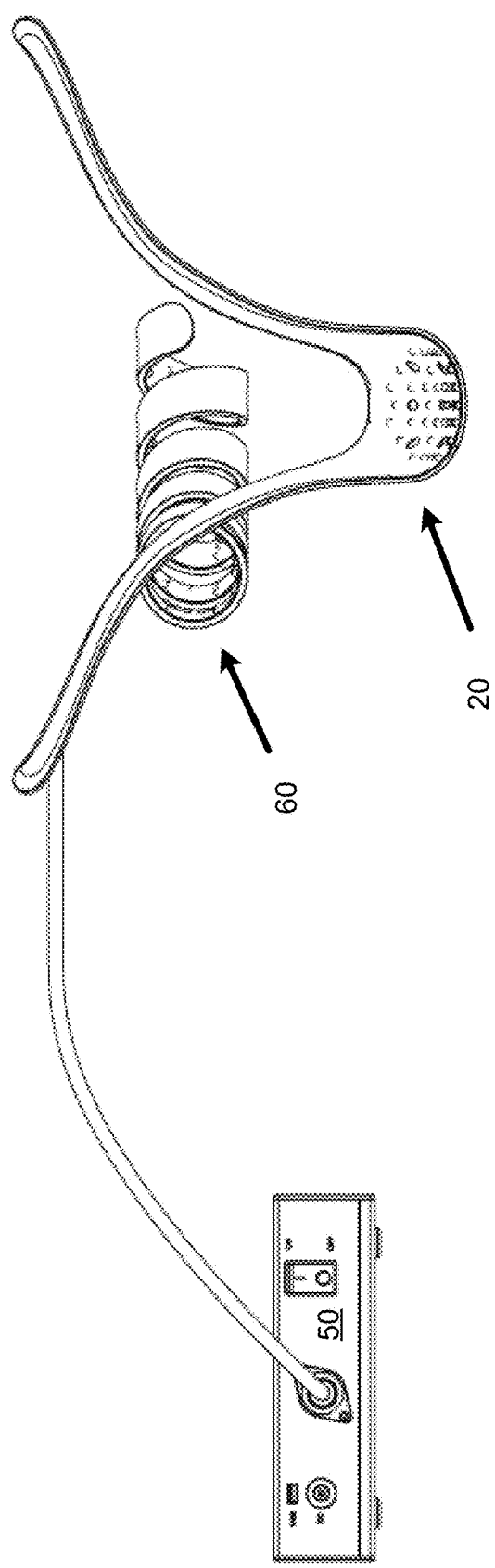
FIG. 14 shows a back view of the device of FIG. 8.
Figure 15:
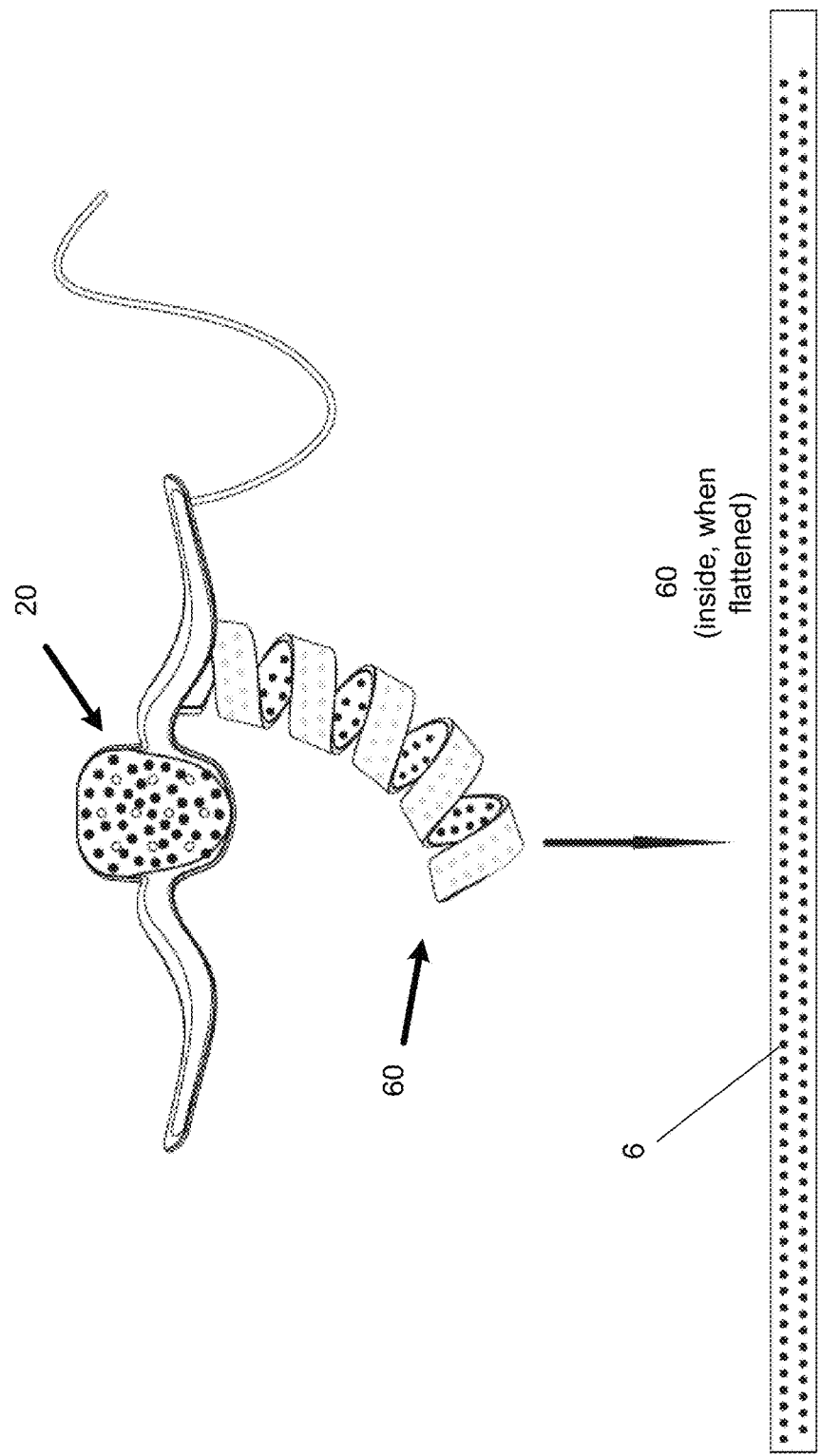
FIG. 15 shows a top view of the device of FIG. 8 with an alternative light source pattern.
Figure 16:
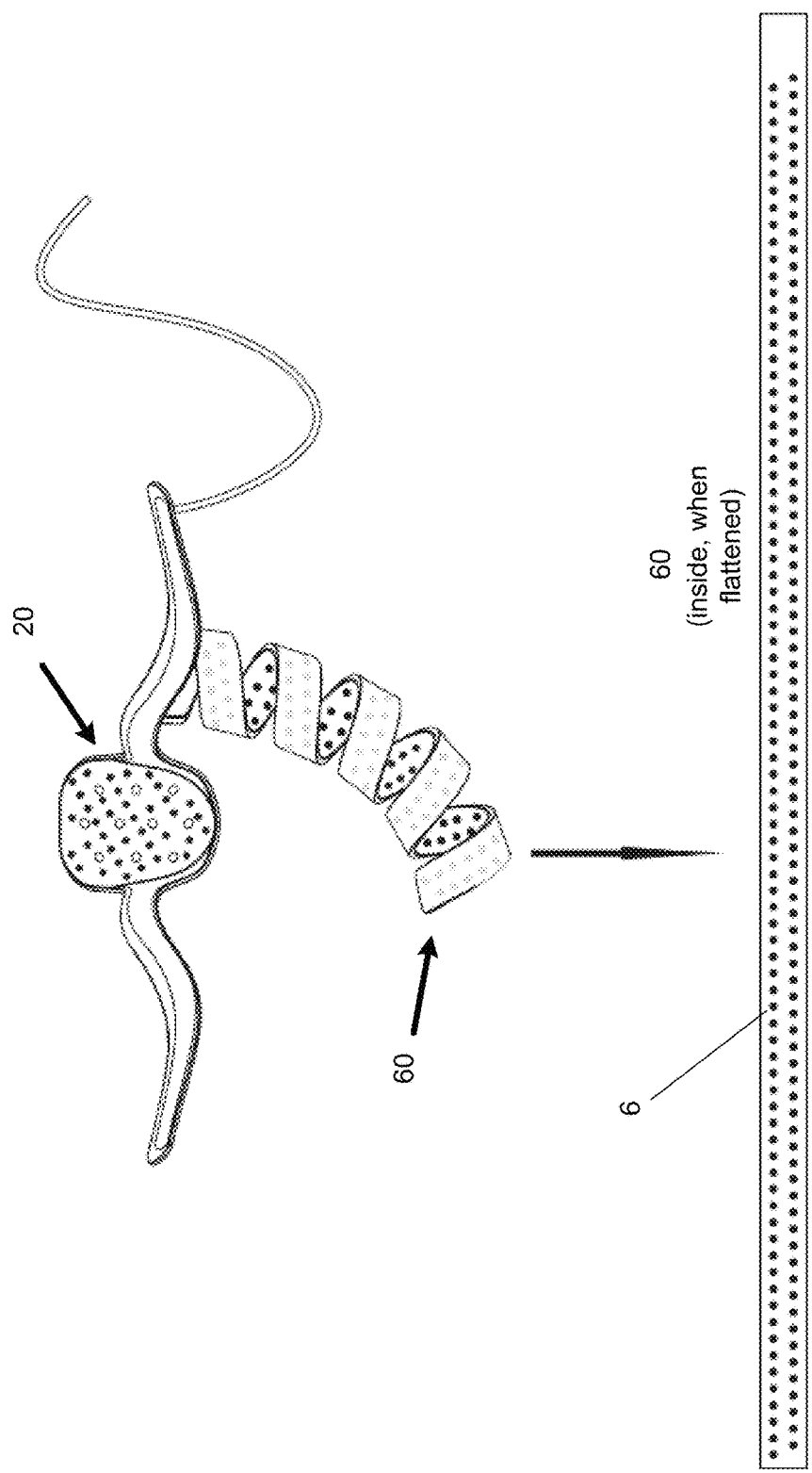
FIG. 16 shows a top view of the device of FIG. 8 with an alternative light source pattern.
Figure 17:
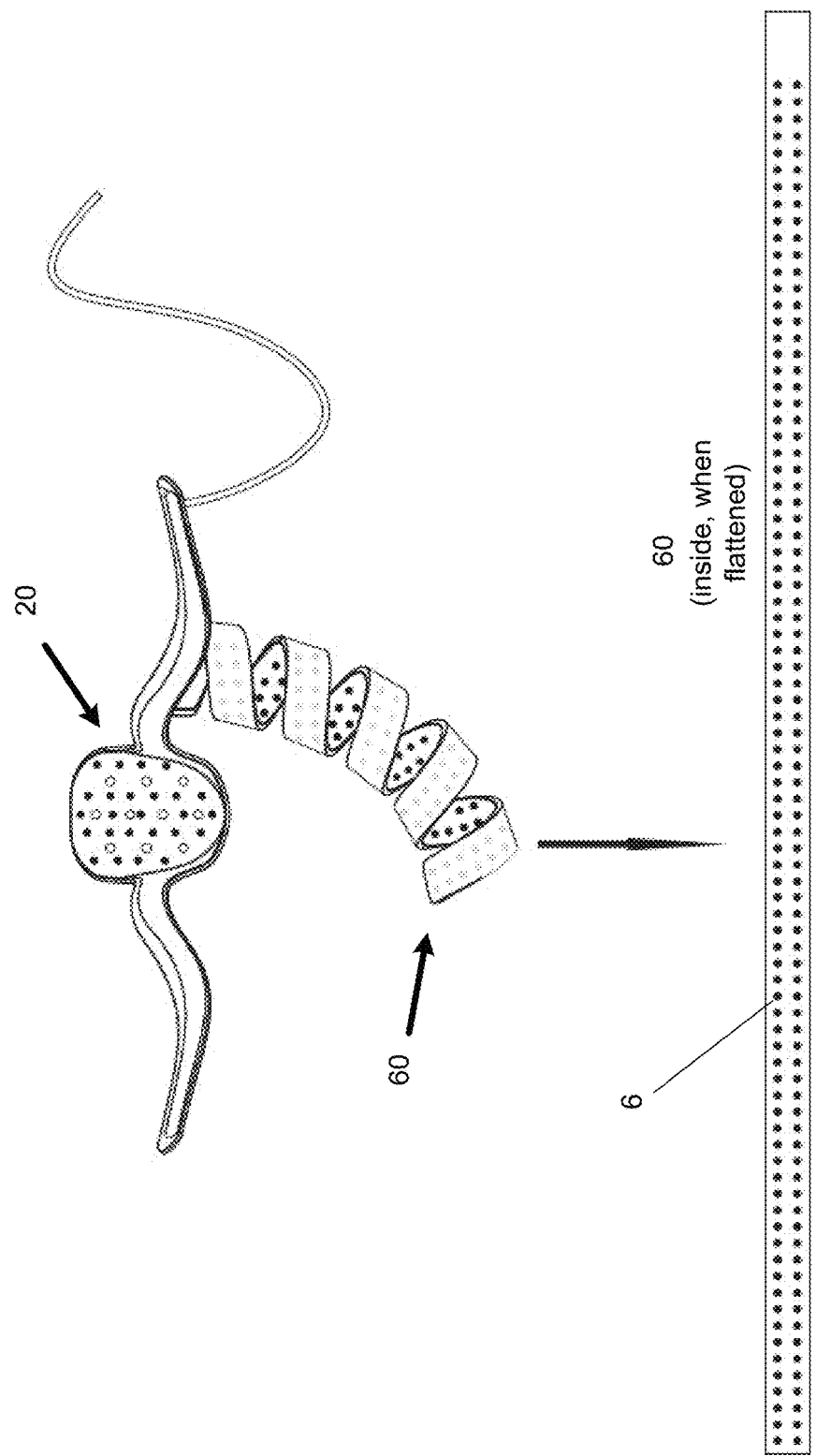
FIG. 17 shows a top view of the device of FIG. 8 with an alternative light source pattern.

In another embodiment, as shown in FIGS. 8-17, the tube has been replaced by a helical or spiral band or ribbon 60, with light sources on the interior, which can be wrapped around the shaft of the male genitalia. The band or ribbon can be freestanding, or attached to the cup 20, or to one of the straps or arms 40.

Figure 18:
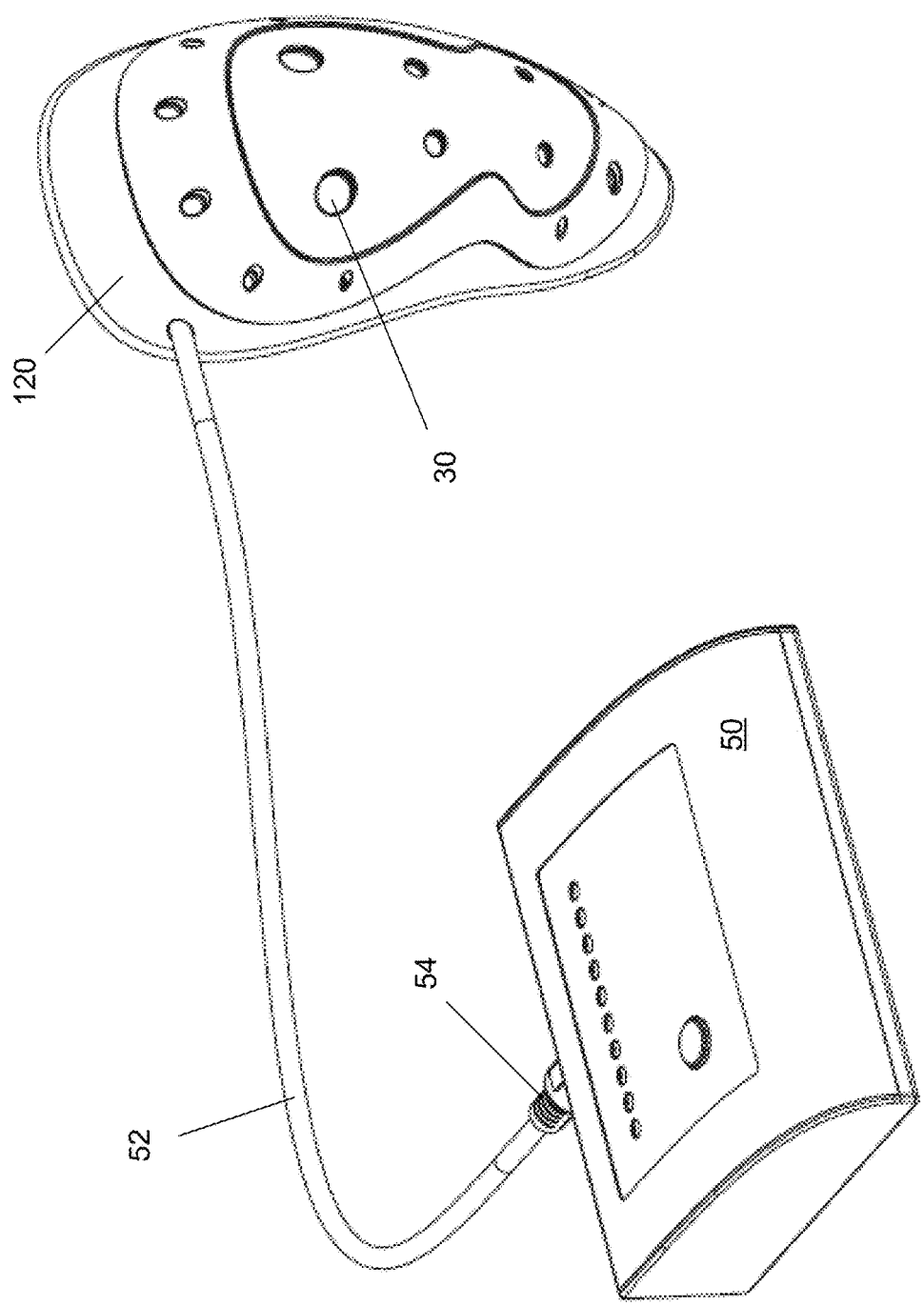
FIG. 18 shows a perspective view of another phototherapy device with cup connected to a control box, in accordance with an embodiment of the present invention.
Figure 19:
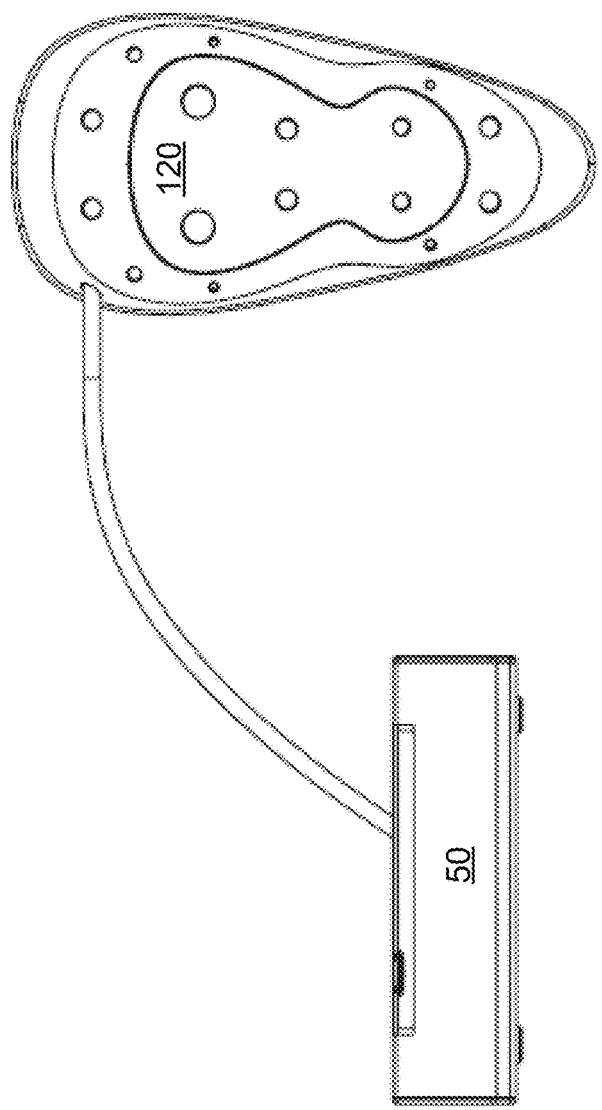
FIG. 19 shows a front view of the device of FIG. 18.
Figure 20:
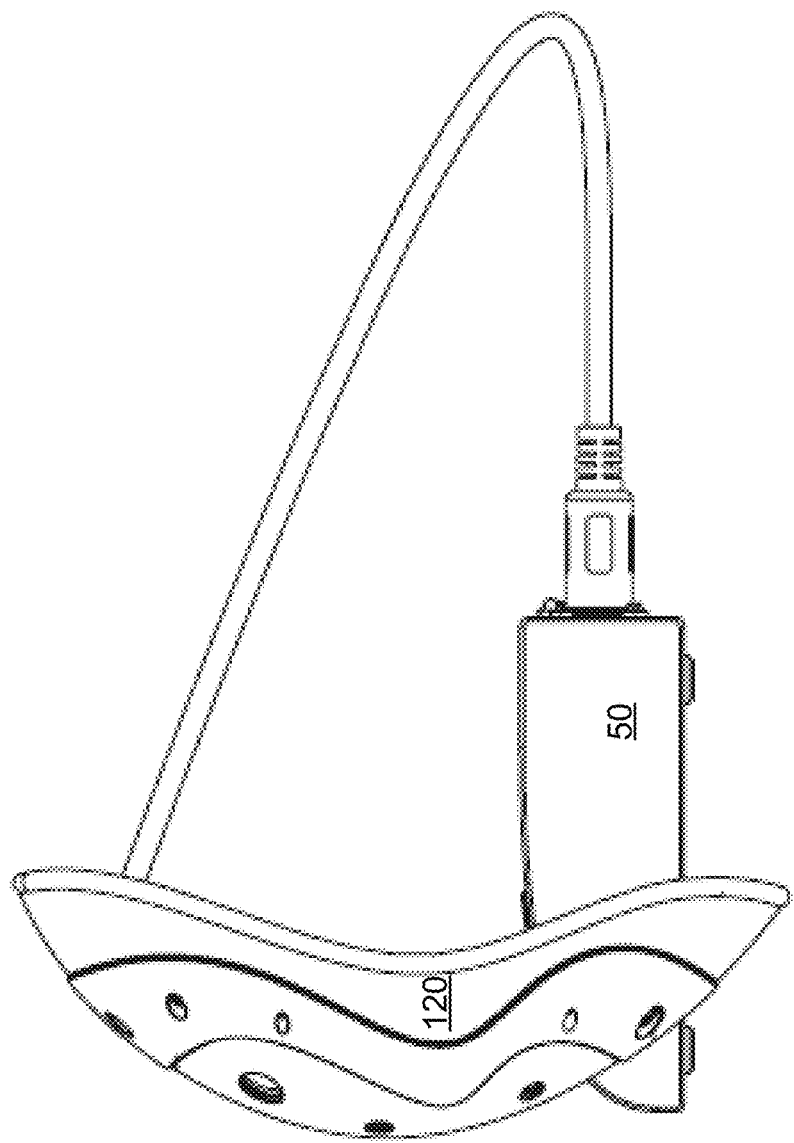
FIG. 20 shows a left side view of the device of FIG. 18.
Figure 21:
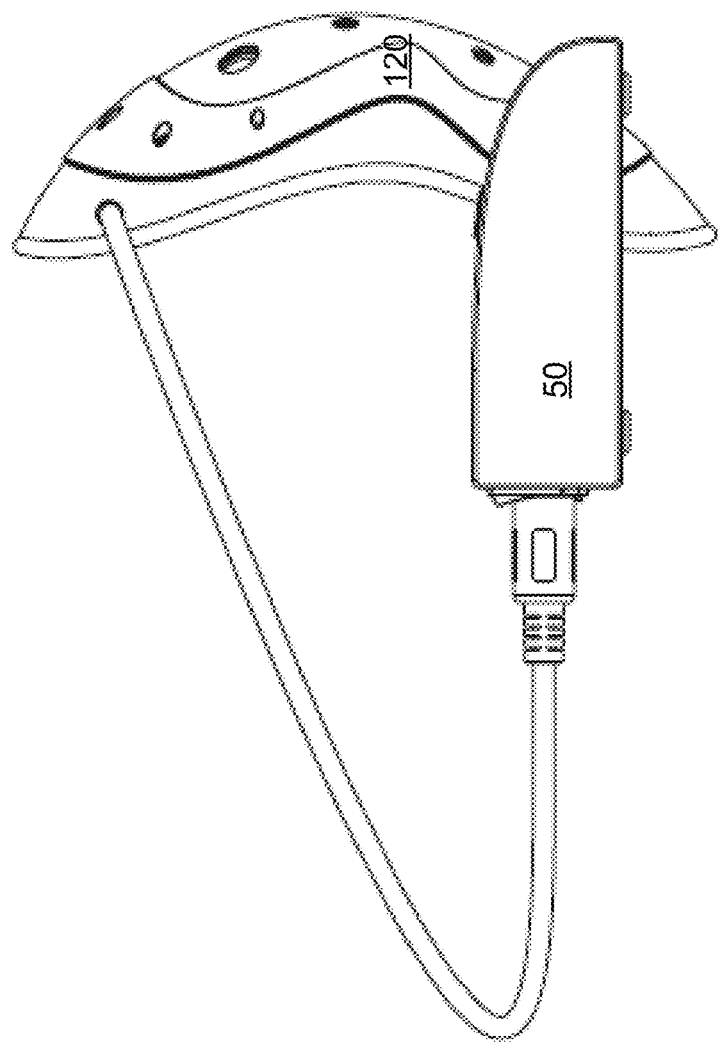
FIG. 21 shows a right side view of the device of FIG. 18.
Figure 22:
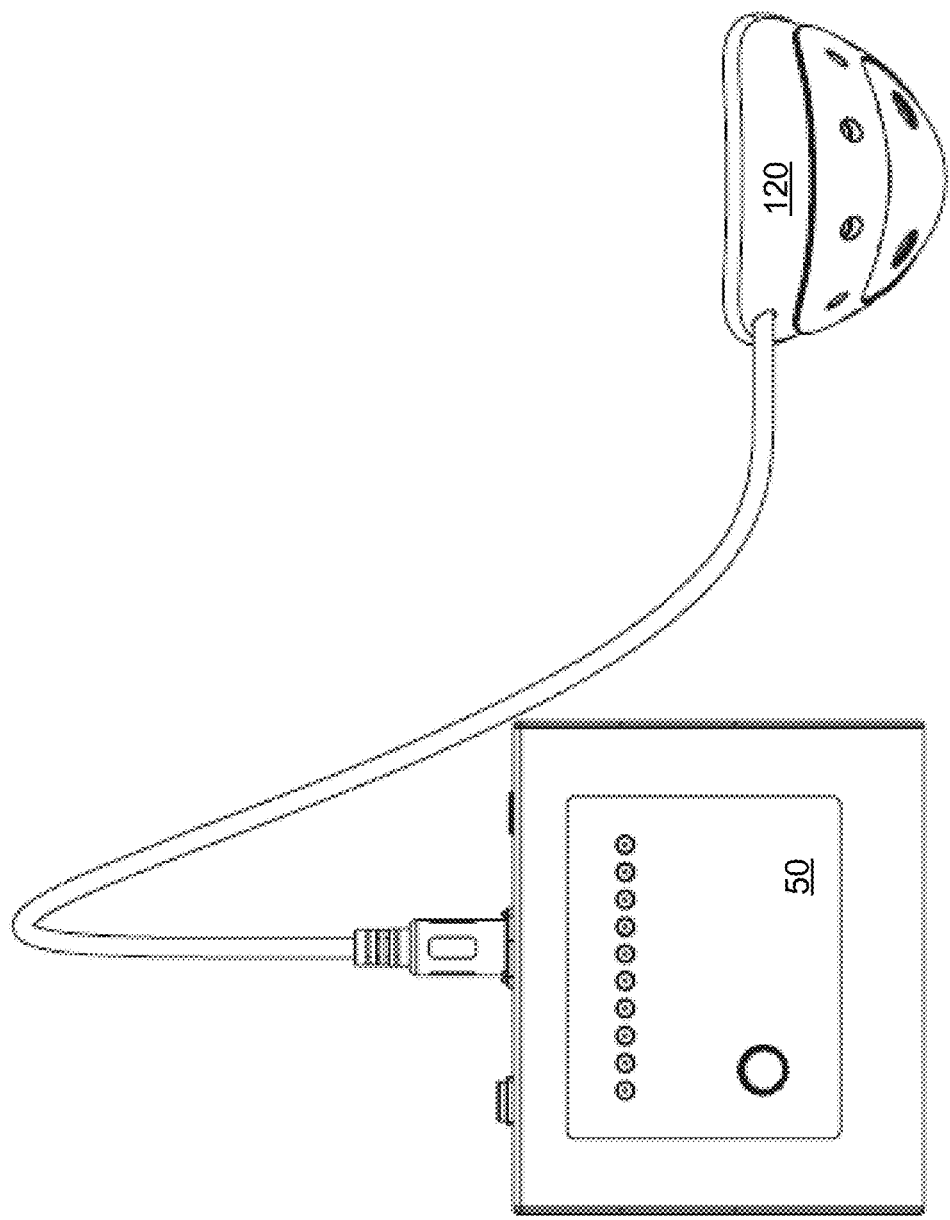
FIG. 22 shows a top view of the device of FIG. 18.
Figure 23:
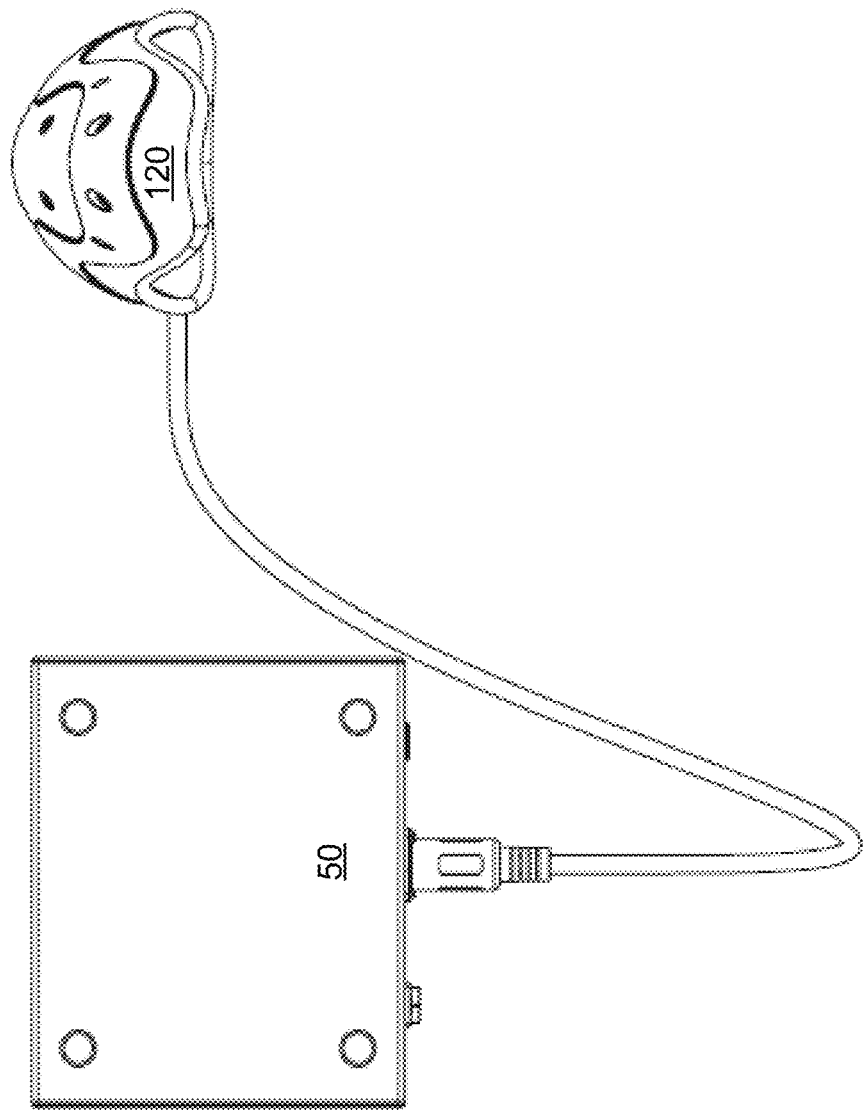
FIG. 23 shows a bottom view of the device of FIG. 18.
Figure 24:
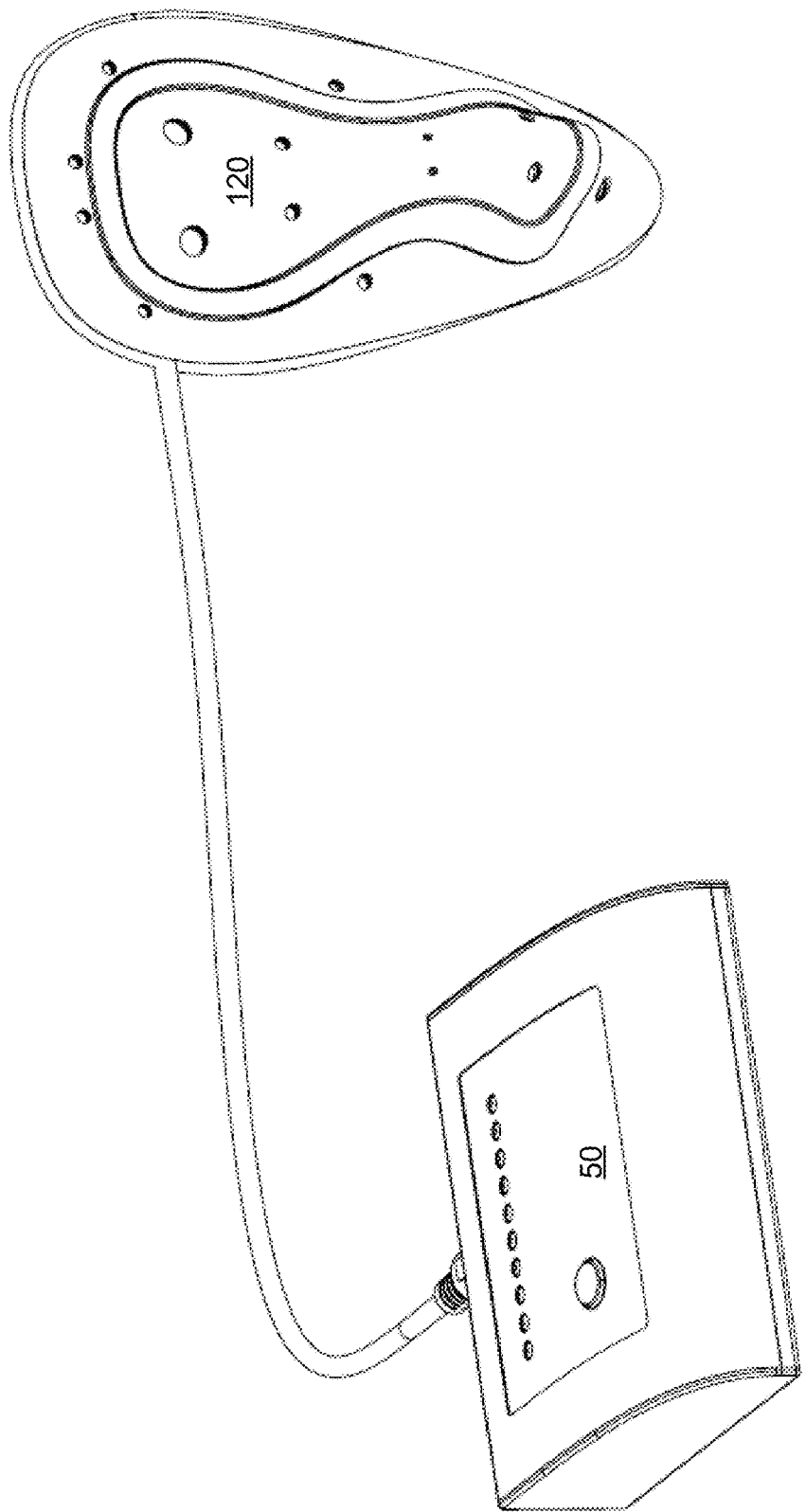
FIG. 24 shows a perspective view of another embodiment of a cup connected to a control box.
Figure 25:
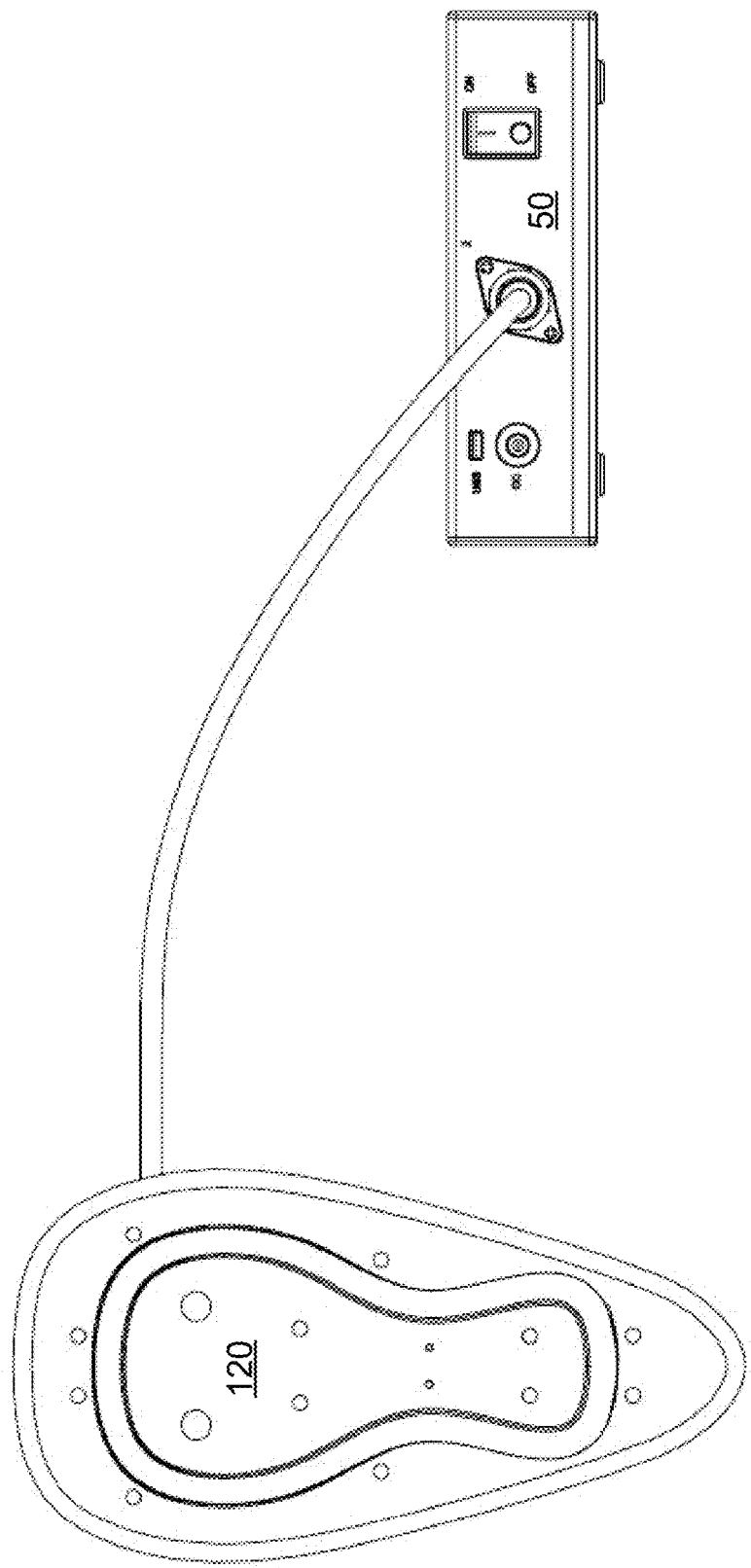
FIG. 25 shows a front view of the device of FIG. 24.
Figure 26:
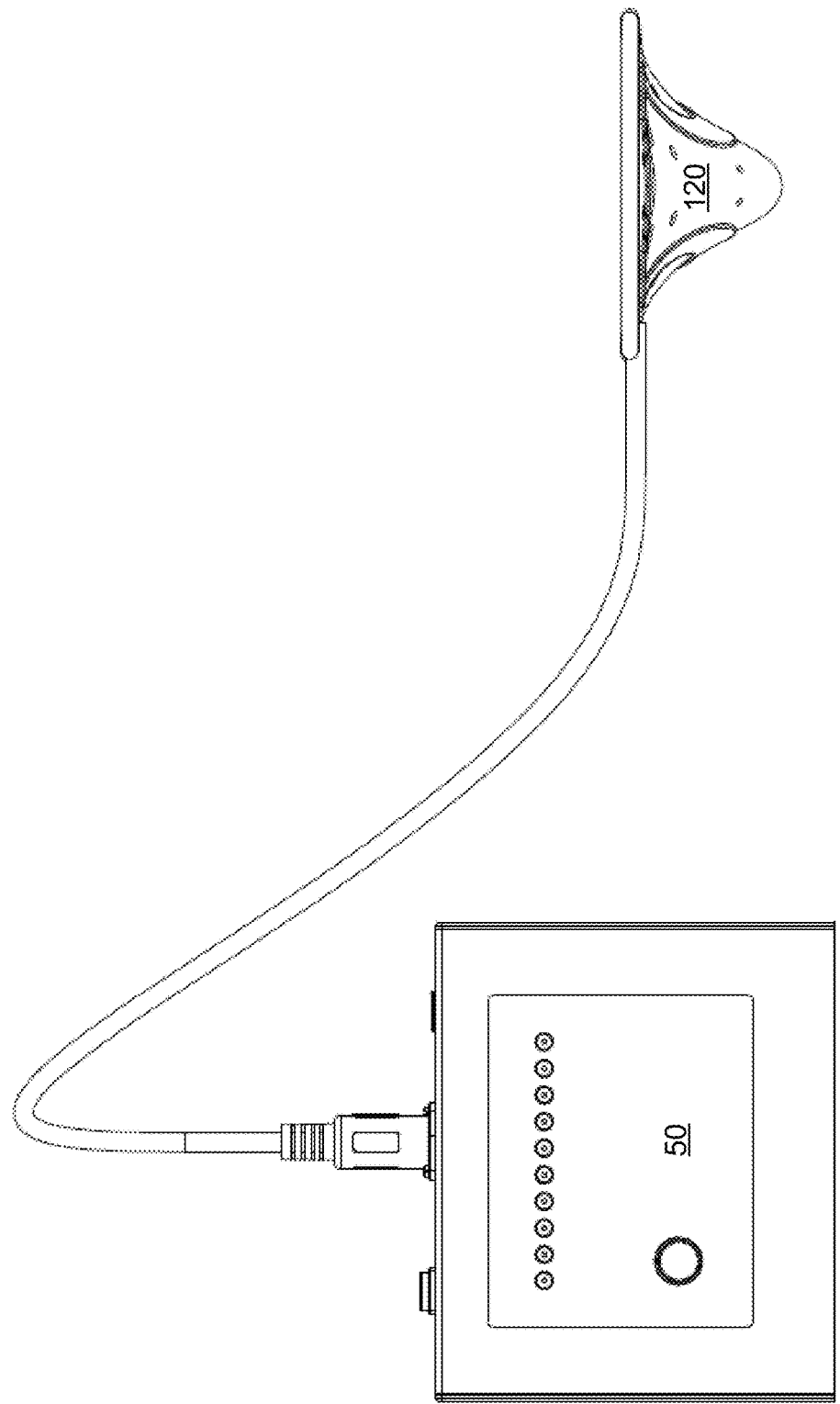
FIG. 26 shows a top view of the device of FIG. 24.
Figure 27:
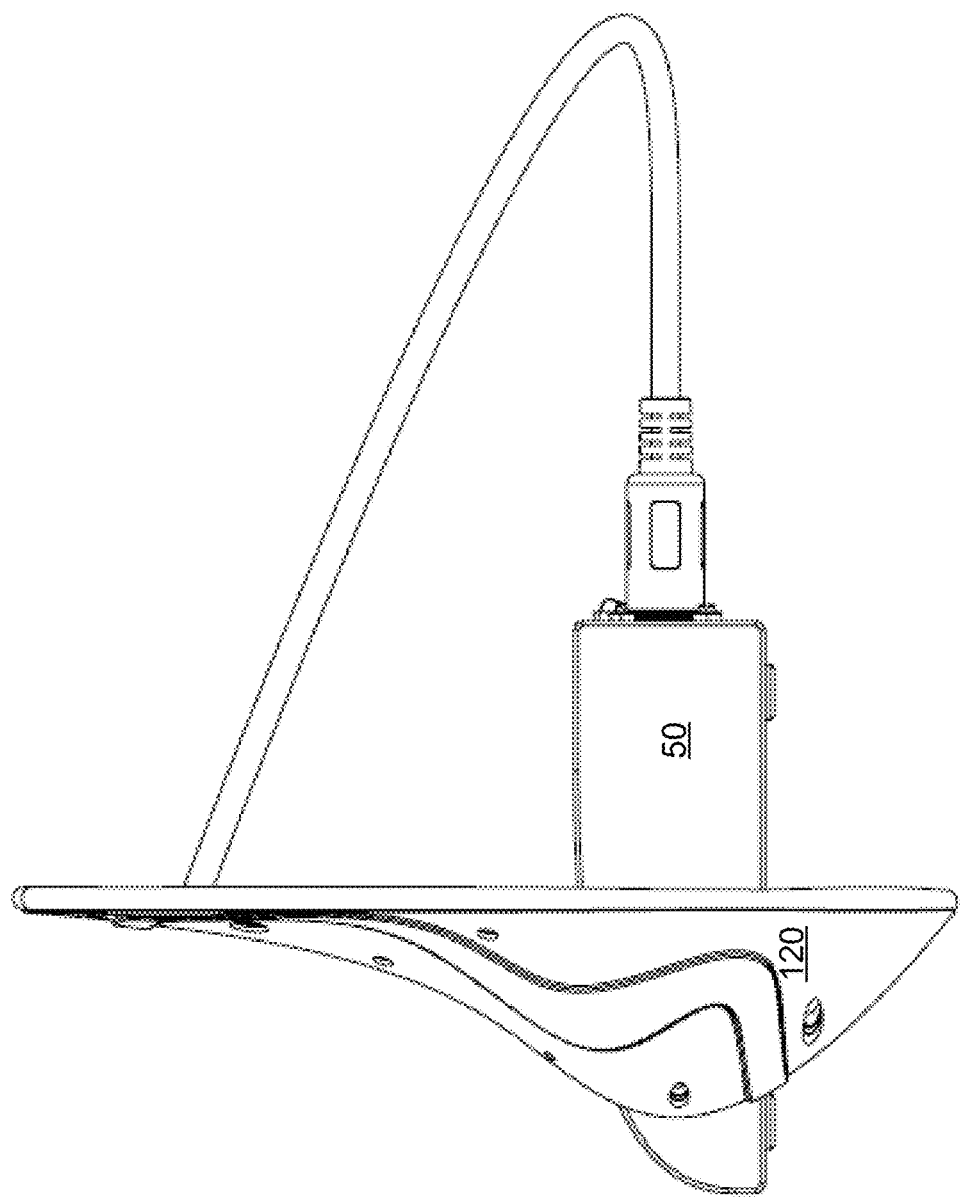
FIG. 27 shows a left side view of the device of FIG. 24.
Figure 28:
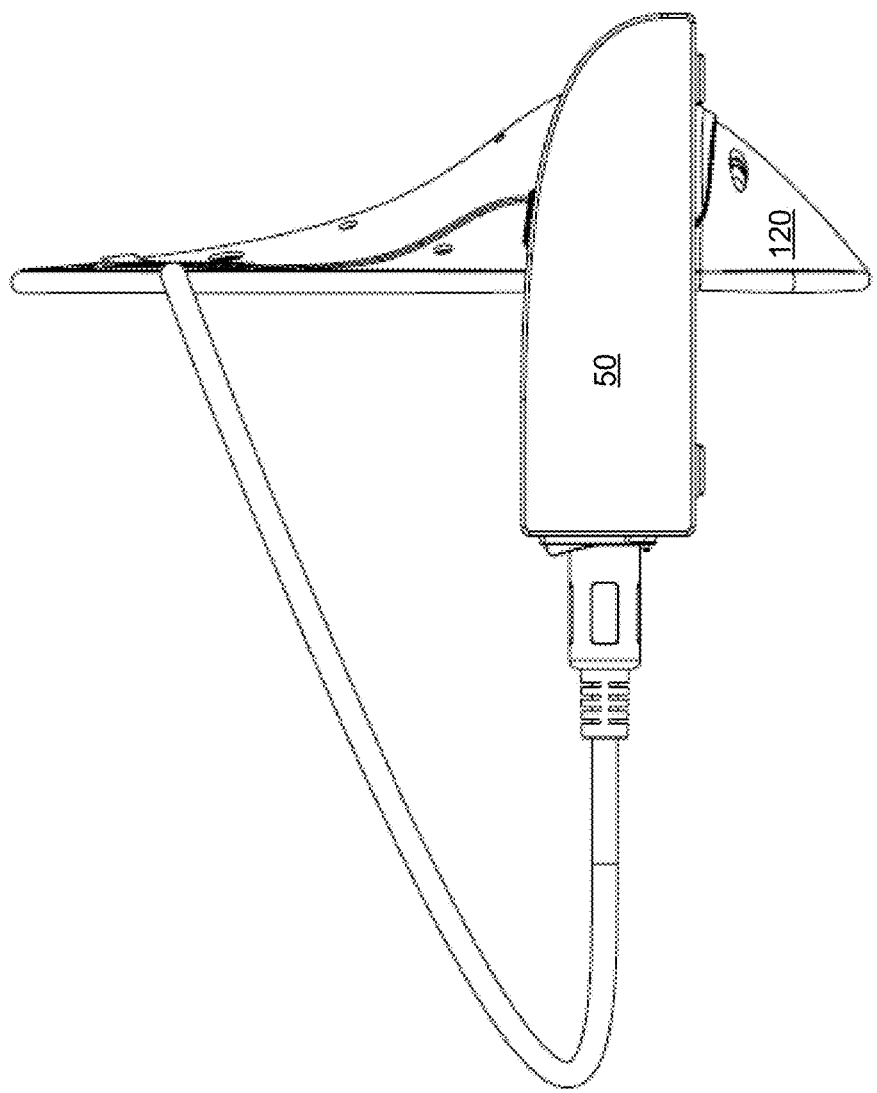
FIG. 28 shows a right side view of the device of FIG. 24.
Figure 29:
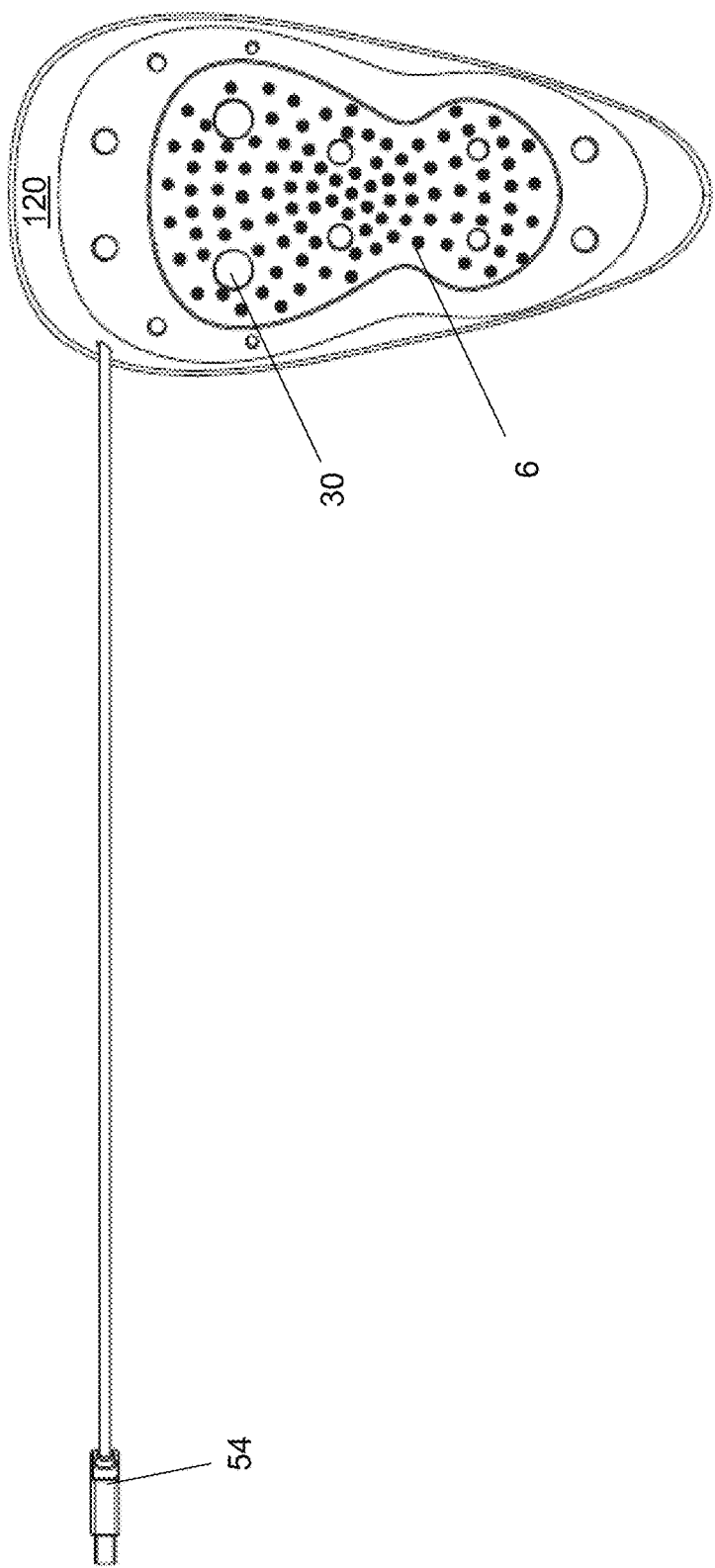
FIG. 29 shows a back view of the device of FIG. 24.
Figure 30:
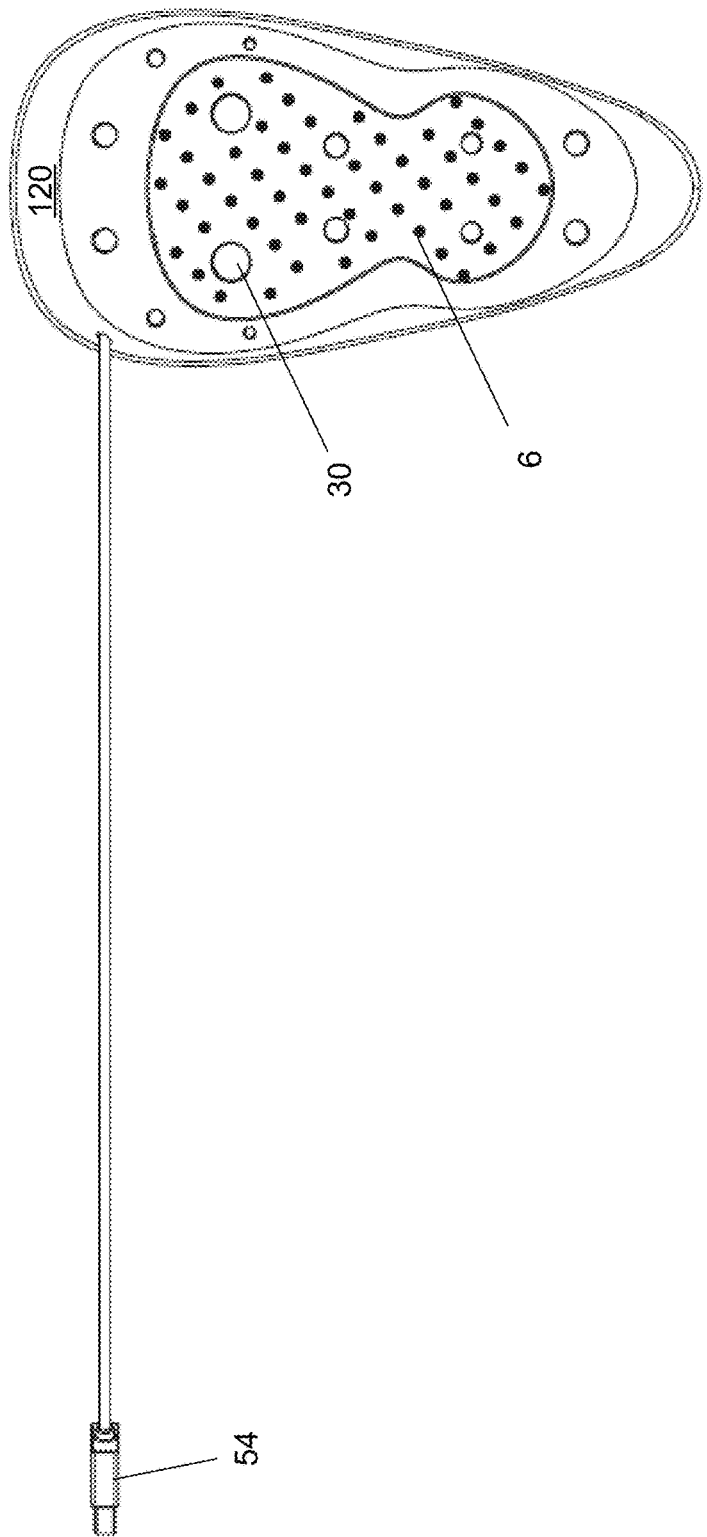
FIG. 30 shows a back view of the device of FIG. 24 with an alternative light source pattern.
Figure 31:
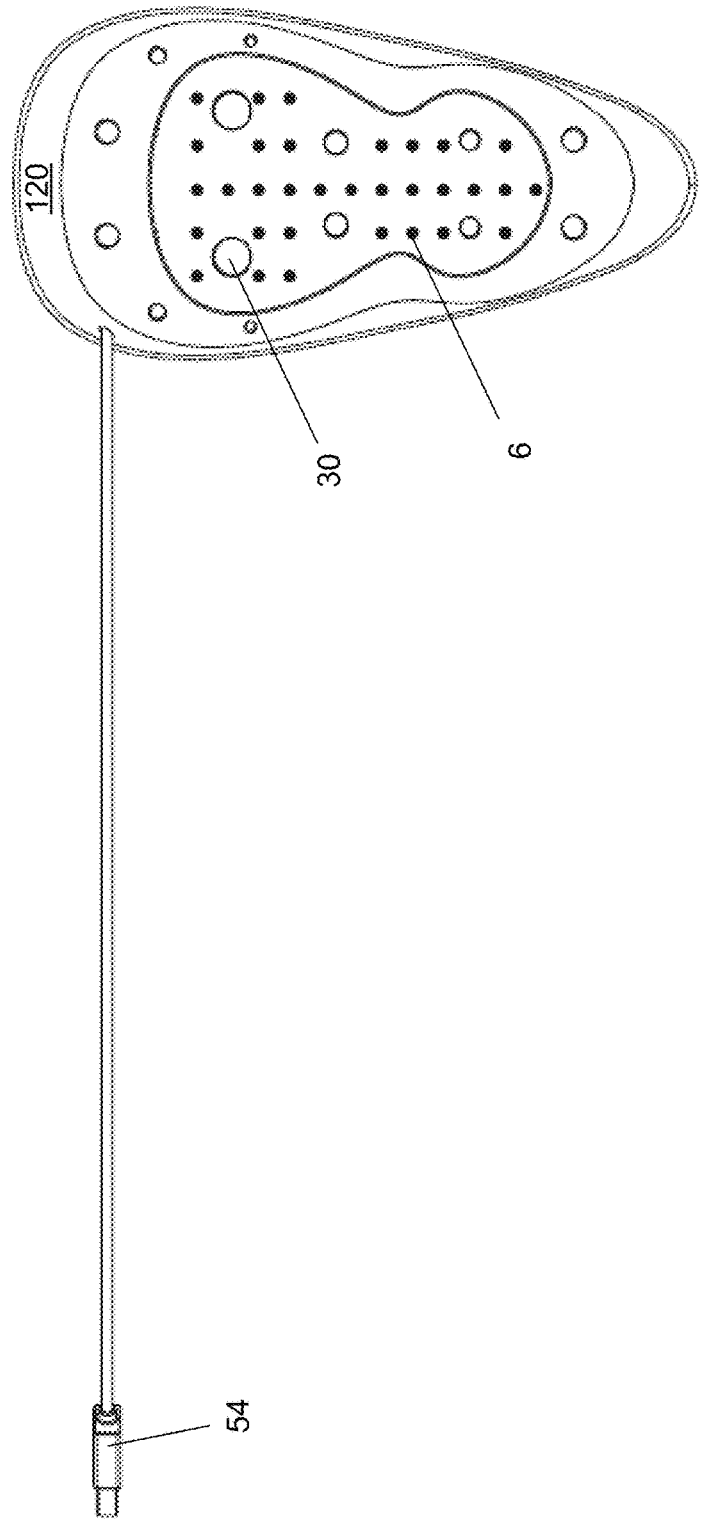
FIG. 31 shows a back view of the device of FIG. 24 with an alternative light source pattern.
Figure 32:
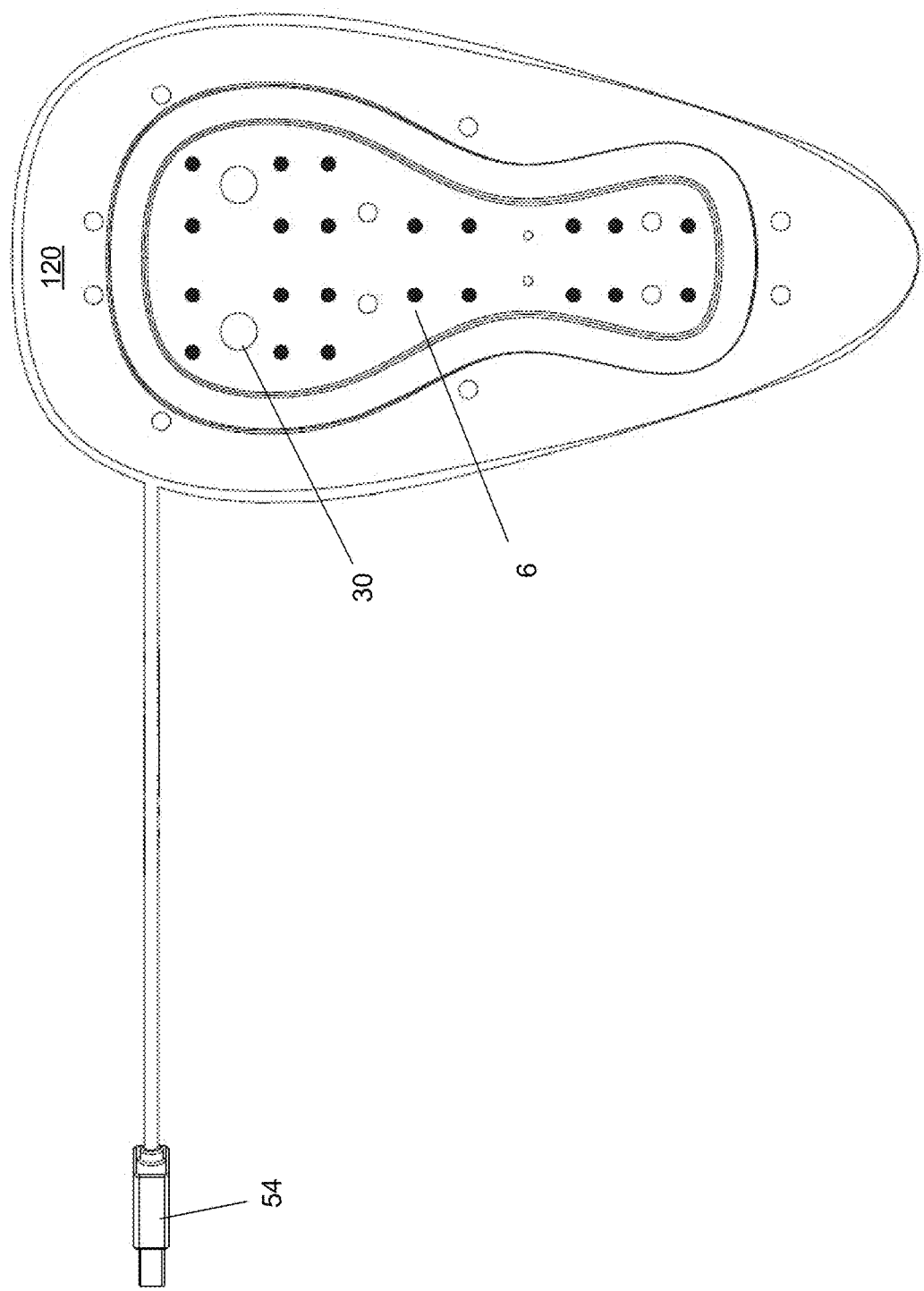
FIGS. 32-34 show back views of a cup with alternative light source patterns.
Figure 33:
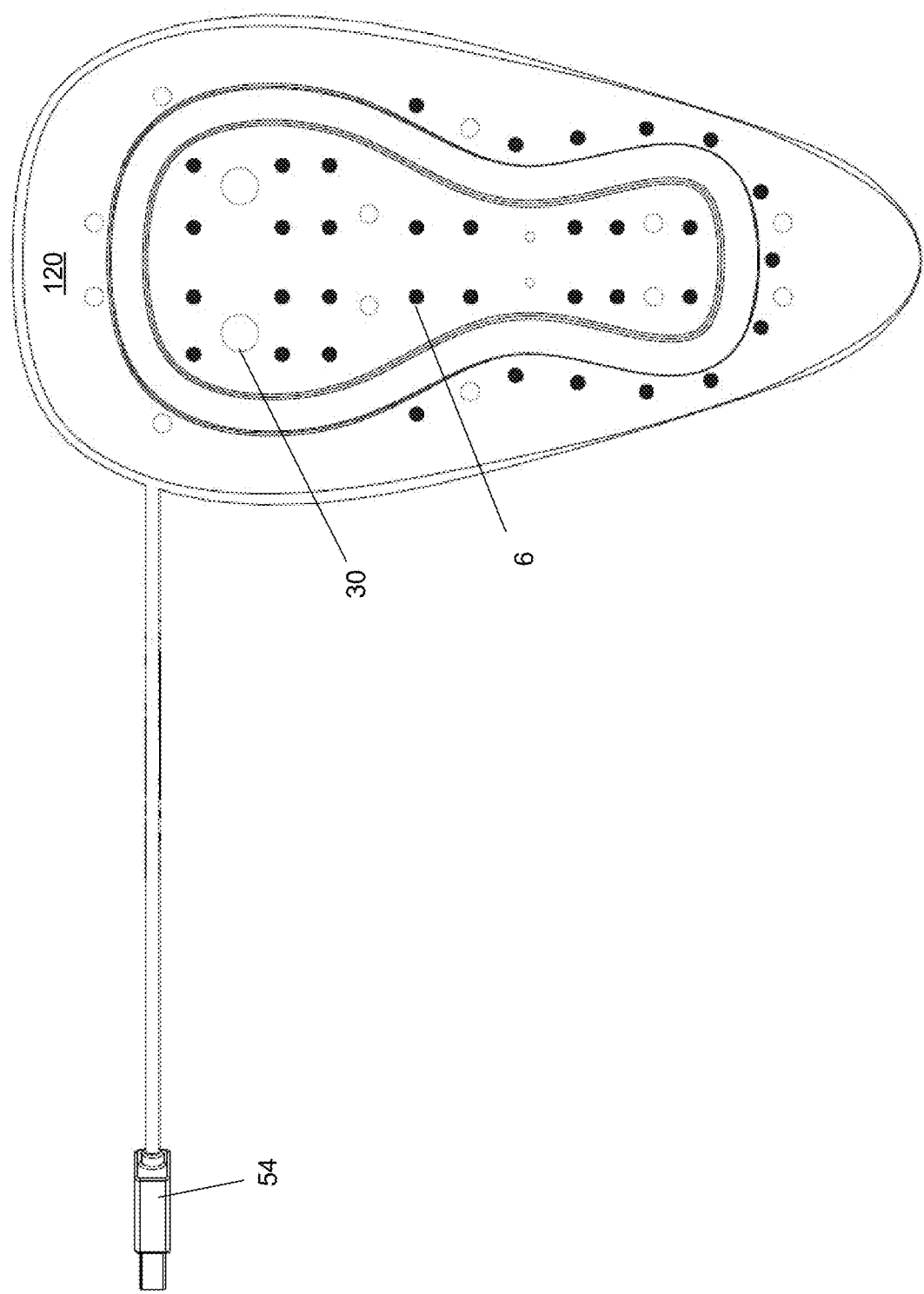
Figure 34:
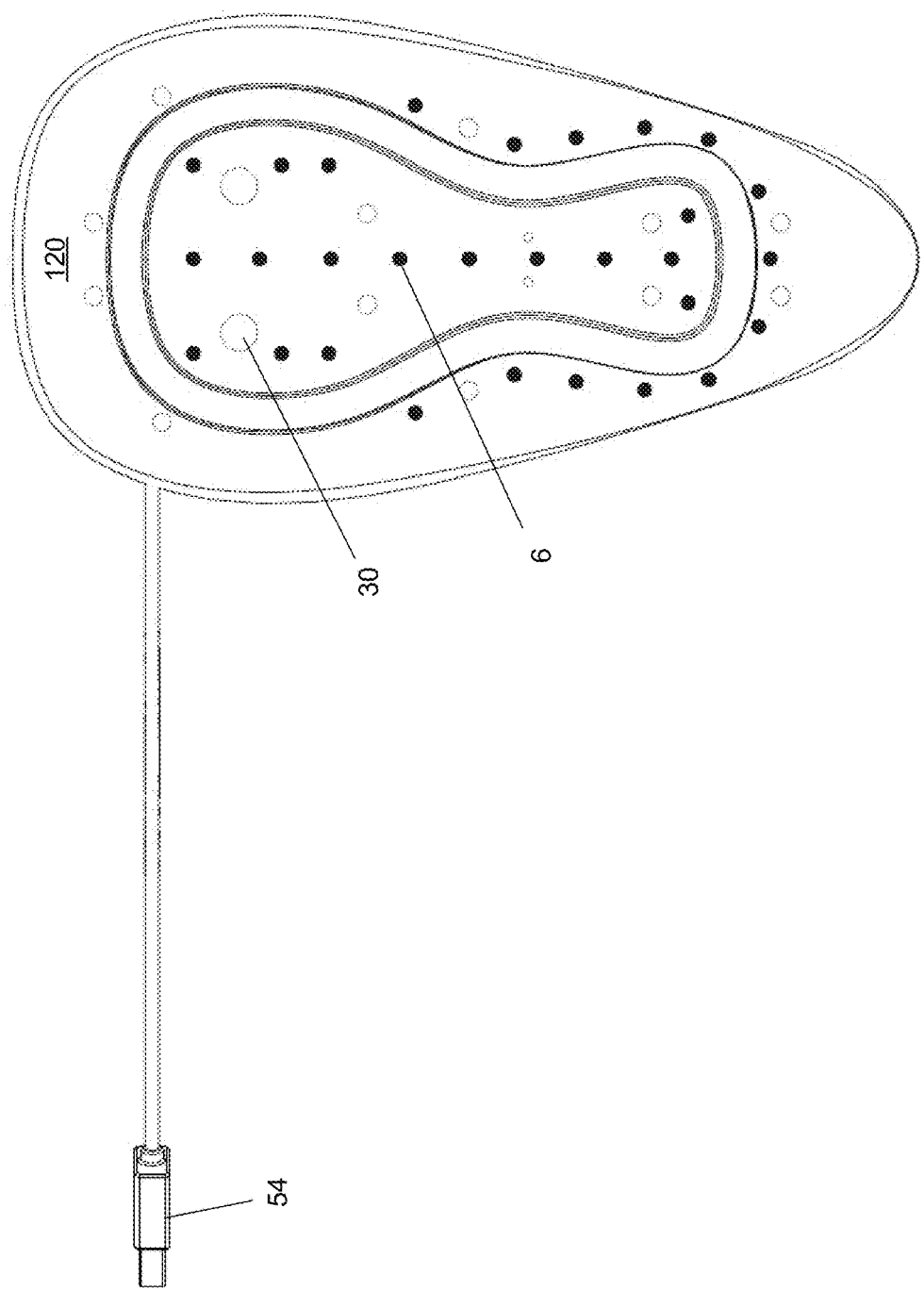

In yet another embodiment, as seen in FIGS. 18-34, the device comprises a single cup 120, into which the entire male genitalia is placed. While this embodiment may not provide as thorough contact with the skin, it may be more comfortable or easier to use for some individuals.

It should be noted that the device may be made of any suitable material, such as plastic, metal, steel, rubber, fabric, or any combination thereof, and may be rigid or flexible in whole or in part. The device may be made in a variety of colors, sizes and configurations. The device may be lined on the interior, such as with a soft foam or the like. There may be various configurations or patterns of light sources, in a variety of colors and intensities (i.e., milliwatt range). Different colors may be used for different treatments.

Figure 35:
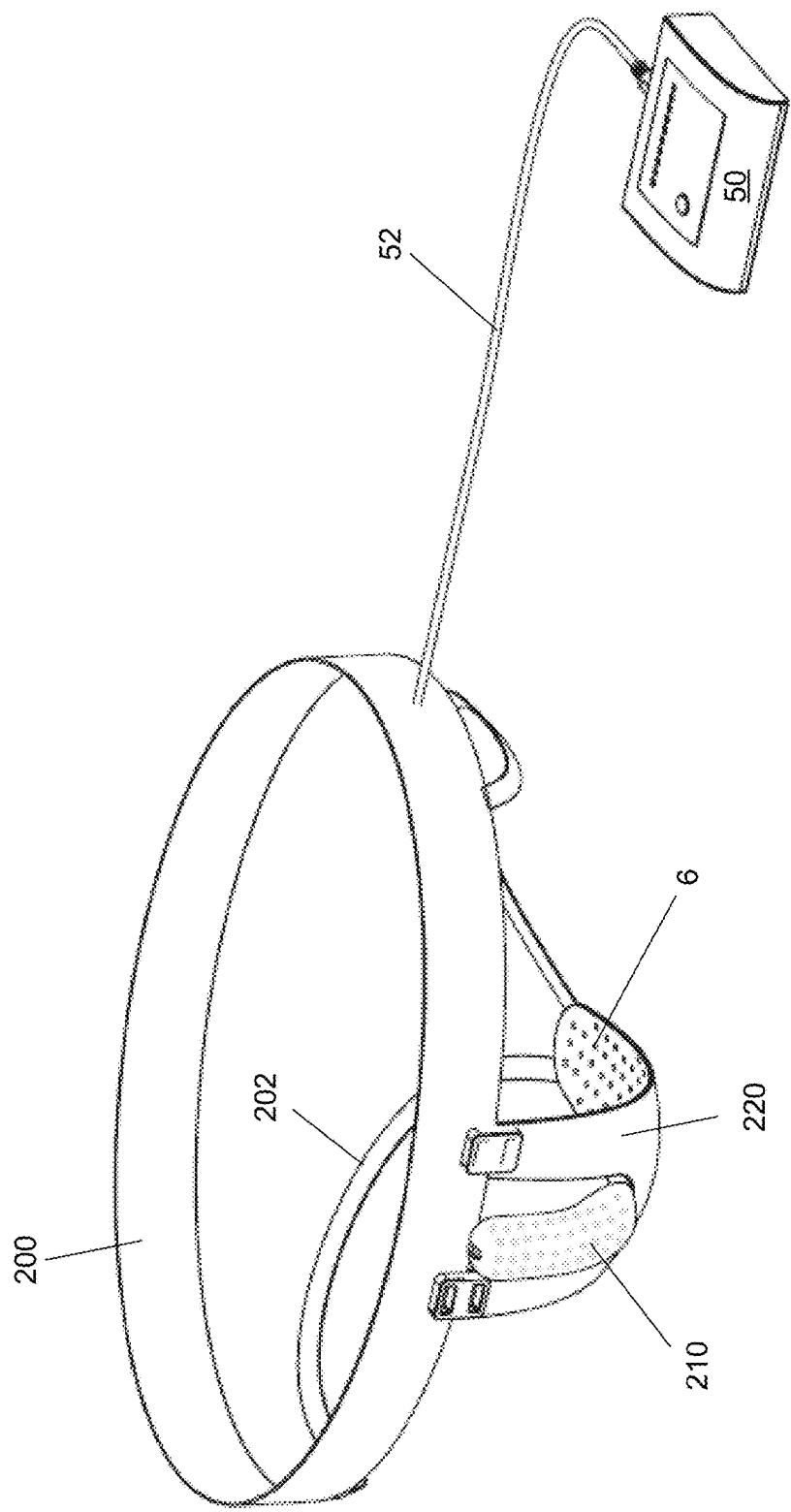
FIG. 35 shows a perspective view of a phototherapy device with tube and cup and support belt connected to a control box, in accordance with an embodiment of the present invention.
Figure 36:
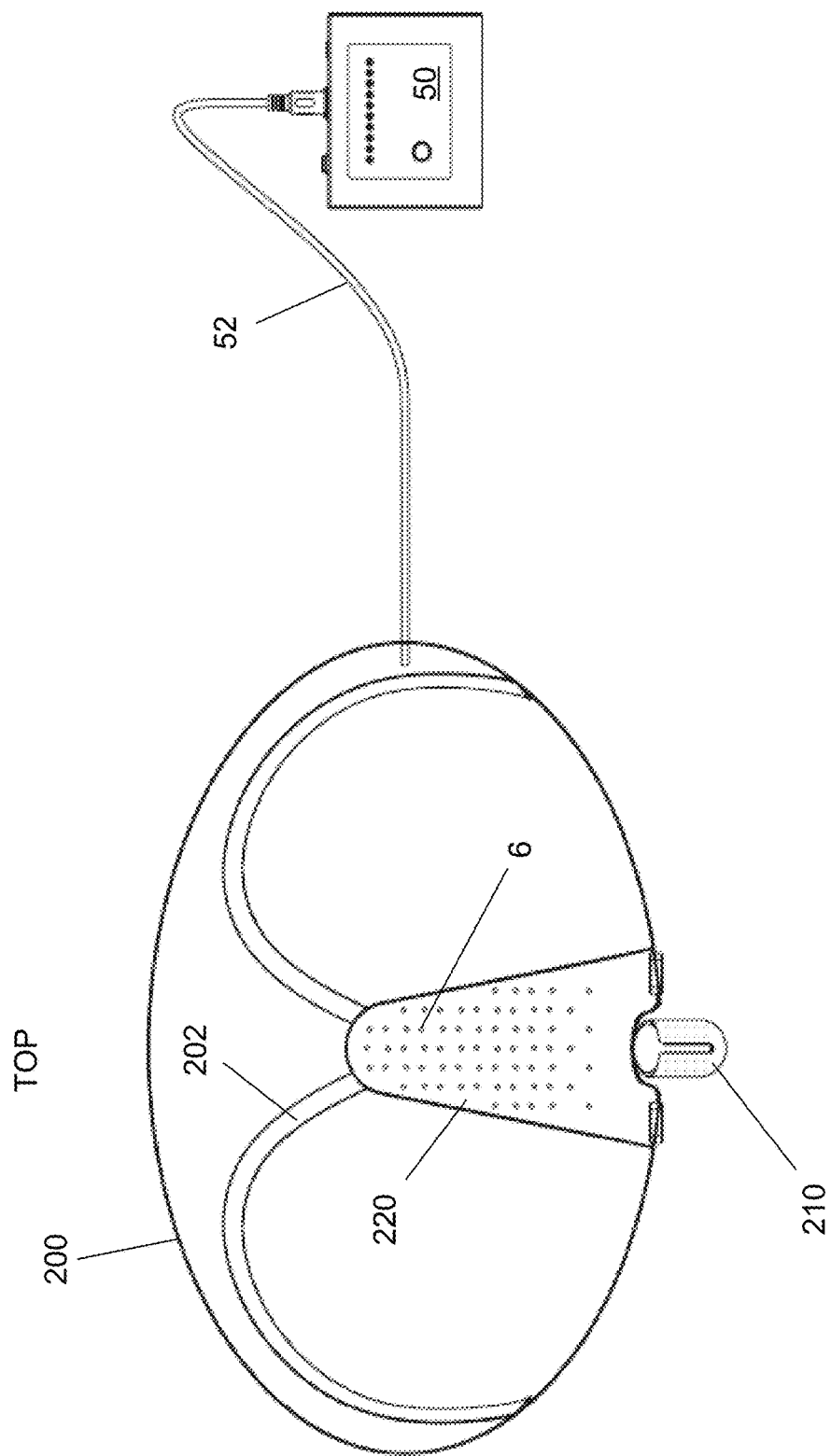
FIG. 36 shows a top view of the device of FIG. 35.
Figure 37:
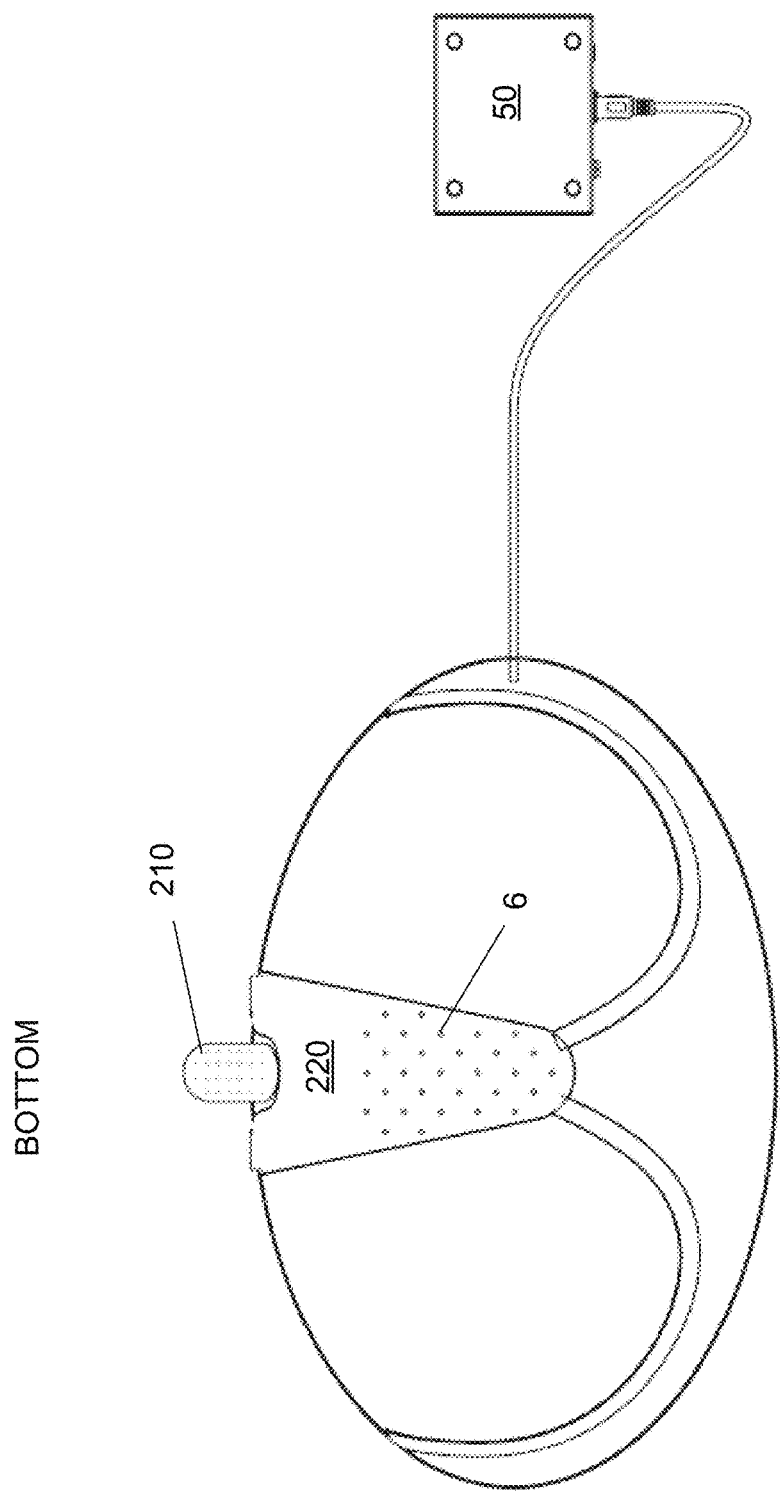
FIG. 37 shows a bottom view of the device of FIG. 35.
Figure 38:
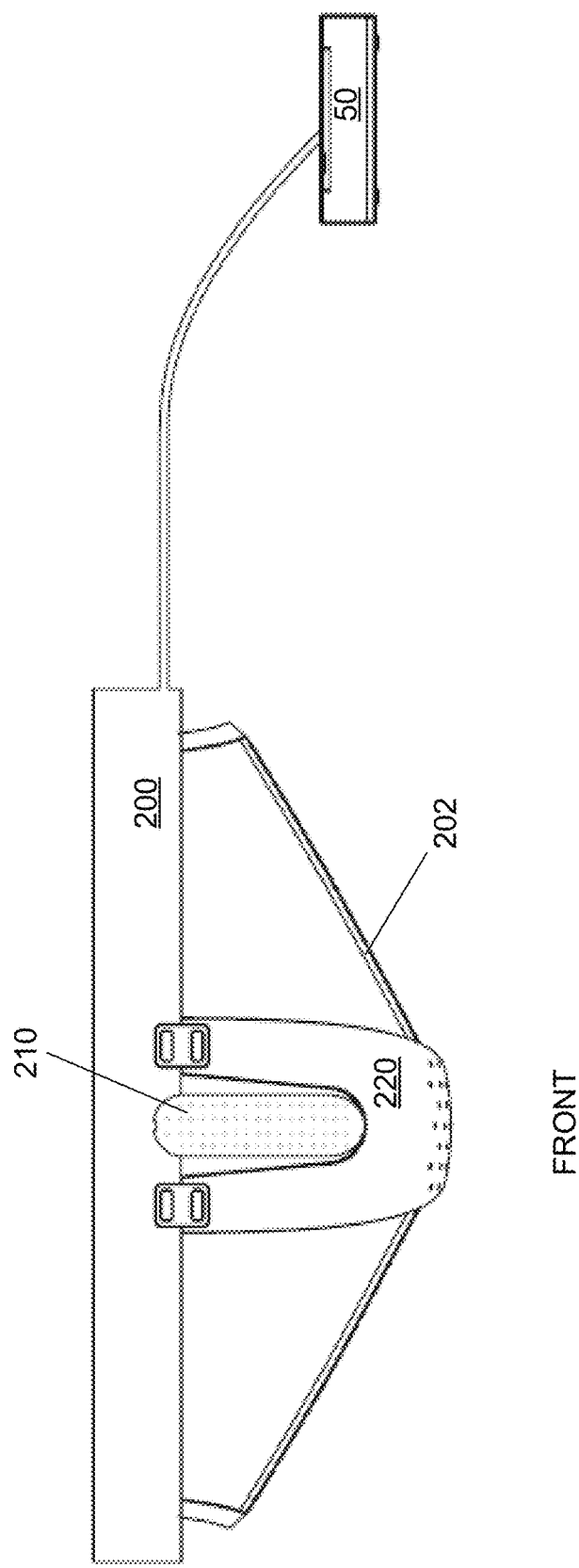
FIG. 38 shows a front view of the device of FIG. 35.
Figure 39:
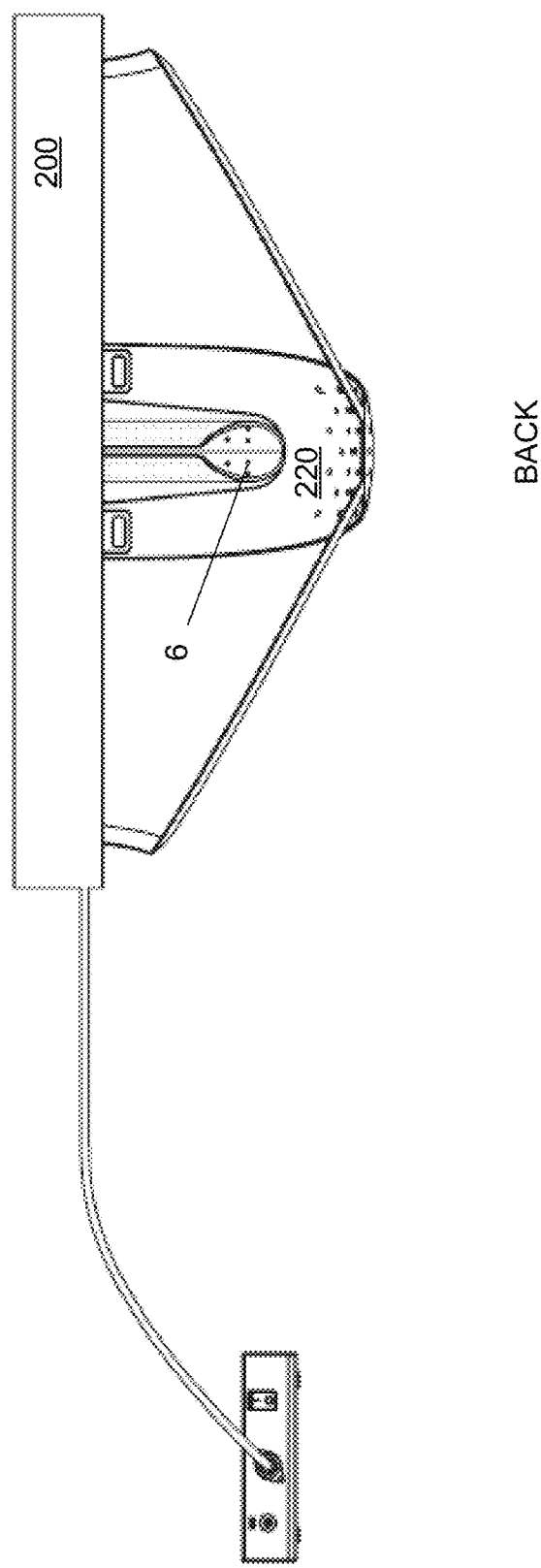
FIG. 39 shows a back view of the device of FIG. 35.
Figure 40:
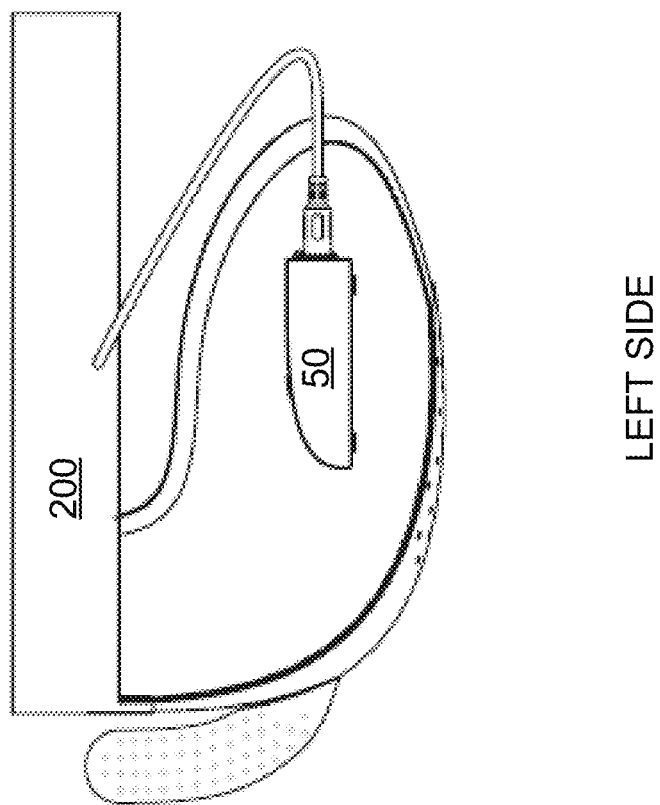
FIG. 40 shows a left side view of the device of FIG. 35.
Figure 41:
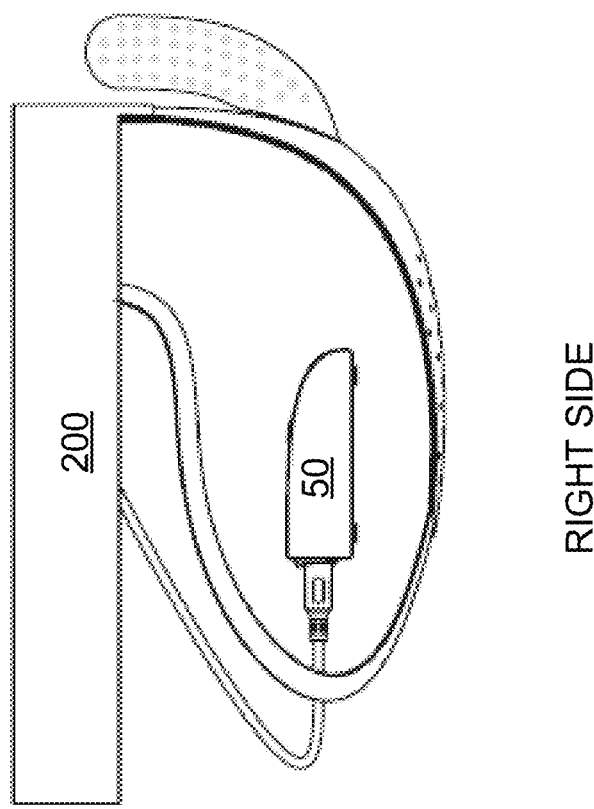
FIG. 41 shows a right side view of the device of FIG. 35.
Figure 42:
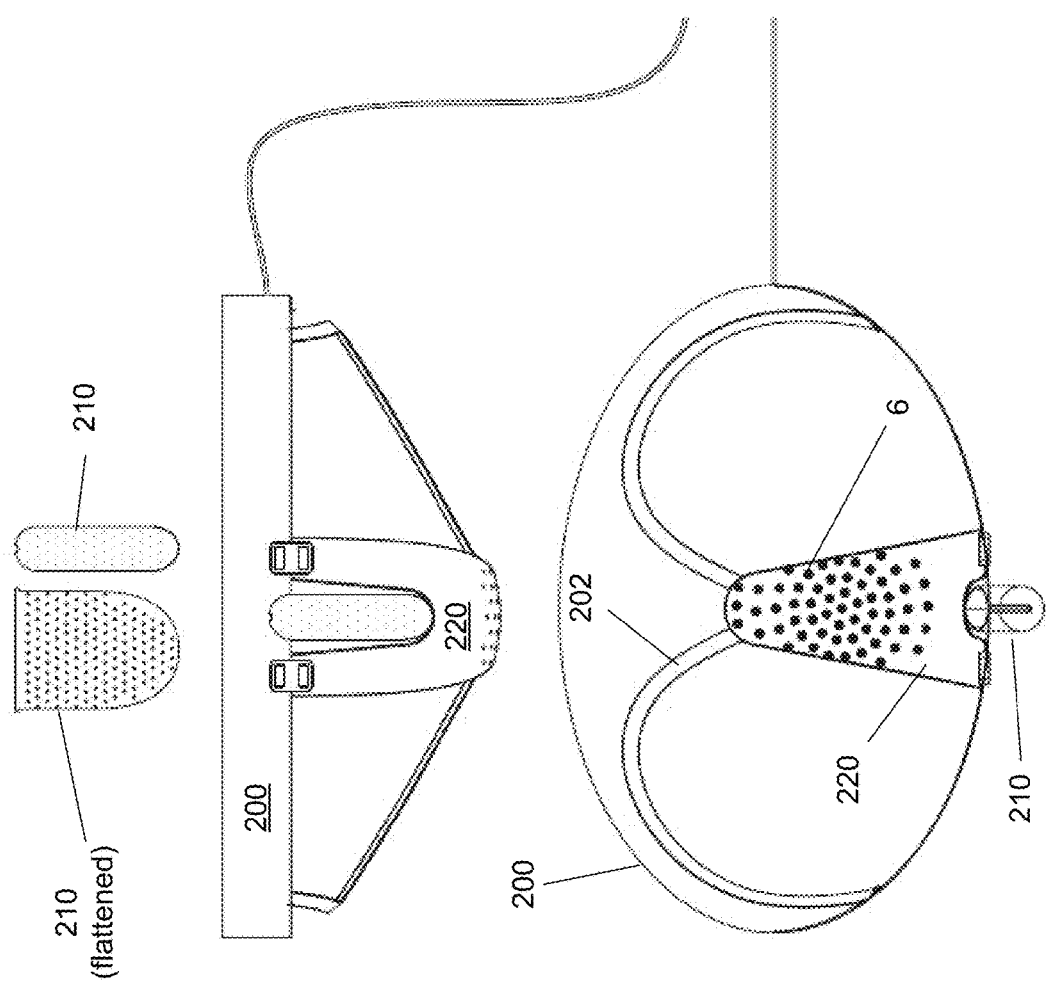
FIGS. 42-44 show views of the device of FIG. 34 with alternative light source patterns.
Figure 43:
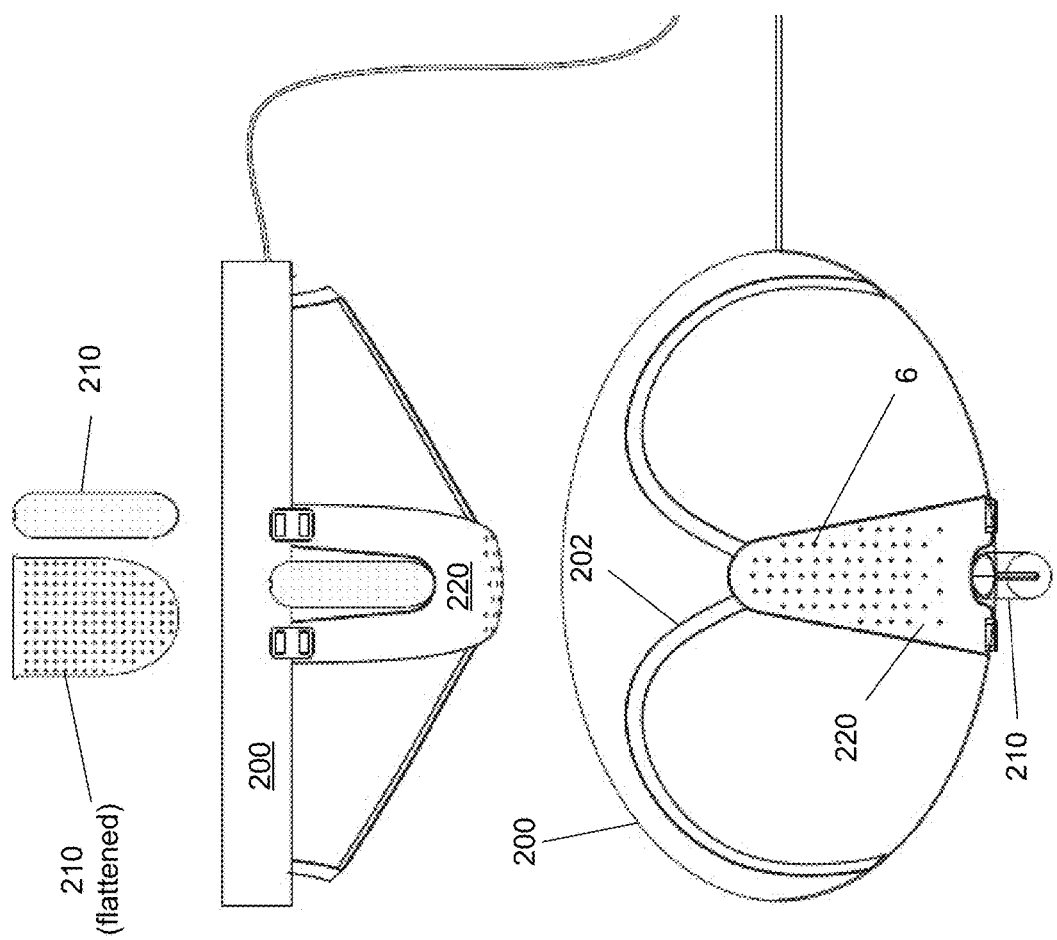
Figure 44:
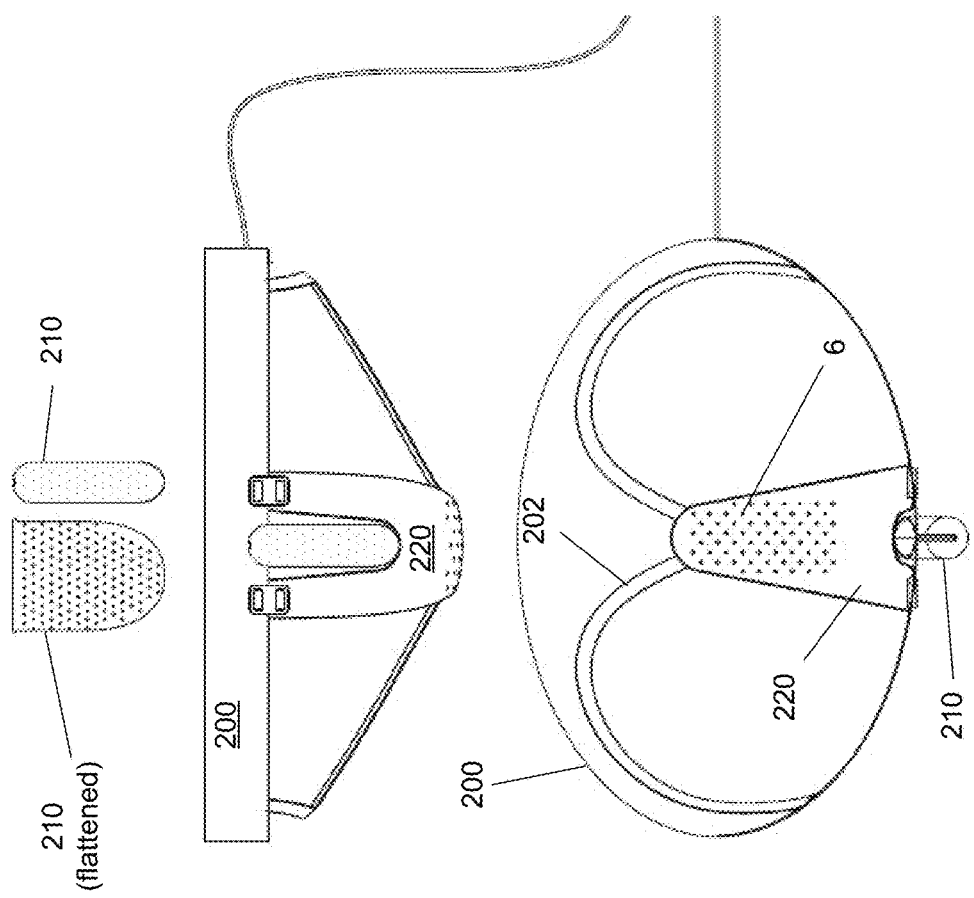

The device may simply be worn underneath underwear, or in a specially-designed support garment, such as a jockstrap, shorts, or belt. FIGS. 35-44 show an example of a support garment comprising a belt or strap 200, which may have leg straps 202, to which a tube 210 and cup or cup-like testicle support 220 are attached (permanently or removably).

The light sources can be controlled by wireless or wired connection with a computing device operating a control program, a touchpad monitor or device on or connected to the cast, or a control unit or box. The user can control color, type, duration, wavelength amplitude, wavelength phase, and frequency (pulse) of the light sources being activated during therapeutic application, as described in further detail below. A control box or control unit suitable for use with the devices described herein is disclosed in U.S. Provisional Application No. 61/835,744, which is incorporated herein by specific reference for all purposes.

Power for the invention may be provided by plugging the device into a standard electrical outlet. Alternatively, one or more batteries may be provided.

The device may be made in a variety of colors, sizes and configurations. There may be various configurations or patterns of LEDs or laser diodes, in a variety of colors and intensities (i.e., milliwatt range). Different colors may be used for different treatments.

In one embodiment, RGB technology utilizes the color mixing properties of red, green, and blue LED chips that are provided on a reflector. A photomixing material and filler resin scatters the light rays to uniformly combine the rays emitted from the LED chips. The photomixing material and filler resin are applied onto upper sides of the light emitting diode chips while being mixed with each other, and the photomixing material is uniformly dispersed in the filler resin.

In several embodiments, the light sources include red, blue, green and orange colors. These colors have the following effects:
- Red: stimulates vitality and growth; good for fatigue and debilitating conditions; use for deficient nutrition, dormant conditions, poor appetite, constipation, depression, drowsiness, and paralysis.
- Blue: slows down growth; calming; acts as a sedative; relieves excitement and inflammation; resets "biological clock" of the human body using doses of 20 minutes; blue light to Alzheimer's patients helped biological clock to sleep longer at night; use for nervousness, irritability, fussiness, feverishness; apply to all conditions where inflammation is present; use for internal bleeding, nervous conditions.
- Green: slows down growth; calming; relieves excitement and inflammation; useful when combined with blue/red and yellow as a brain/nerve stimulate and laxative.
- Orange: a combination of red and yellow is powerful in colds and sluggish/chronic conditions as it helps release stored energy.

In one embodiment, the invention can run any light frequency within the pulsing range of 0 Hz to 100,000,000,000 Hz, and can run all safe wavelengths of the electromagnetic spectrum, including visible light and near-infrared light. In one exemplary embodiment, the power output per laser diode, LED, or fiber optic ranges from 1 mW to 300 mW.

In another exemplary embodiment, the invention produces specific wavelengths in the form of linear waves, including, but not limited to, sine, square, triangular, and saw tooth waves. Additional wave types can be produced, including, but not limited to, solution waves, a self-reinforcing solitary wave (a wave packet or pulse) that maintains its shape while it travels at constant speed, and longitudinal waves capable of passing through tissue from one side to another with no loss of strength. The utilization of a single wave type or combination of wave types produces a wavelength with no degradation to wave shape allowing the energy produced from the wave to penetrate any desired depth of biological tissue.

In a further embodiment, the present invention incorporates the geometric configuration of single light technology or multiple light technologies, wavelength, amplitude and power output, referred to as the array. The geometric configuration is not limited to any single configuration and can include any geometric configuration of wavelengths, power output, amplitude, and wave types. The array is engineered to produce multiple wavelengths, power outputs, amplitudes and wave types producing therapeutic benefits to biological tissue. This is accomplished by utilizing expandable software, smart chips, adaptive lenses, and light producing technology that is completely scalable and configurable to operator needs. The geometric arrangement of the light technology is not limited to any single geometric configuration, wavelength, power output, amplitude, or wave type. The array can be configured to support any geometric configuration of multiple wavelengths, multiple power outputs, multiple amplitudes, or multiple wave types.

Using the applicable control mechanism, in one embodiment the operator or user can control the frequency, amplitude, and phase of the wavelengths through a digital interface. The operator can select the frequency (pulse), wavelength, amplitude, and wave type associated with each light-emitting source. This phase relationship allows for each channel to be specifically programmed with frequency and peak-to-peak amplitude allowing multiple channels to operate at a different frequency (pulse) and amplitude. Thus, the phototherapy device can produce multiple wavelengths, multiple wave types, multiple frequencies (pulses), and multiple amplitudes. It also can be used to provide and control vibrational therapies, including but not limited to sonic or ultrasonic or combinations thereof.

In one particular embodiment, the present invention will only work with specific control boxes, accessories, or computing devices, which can be self-identifying through "handshake" communications technology. Utilizing handshake technology will only pair specific units to specific accessories. A specific circuit board chip may be utilized in each and every piece of equipment. These chips include a one-of-a-kind code that forms a unique link to each other. The circuit board may be a variable frequency circuit board. Specific RF chips may be installed in each and every unit so that identifications can be placed into each piece of equipment to identify purchase dates and other necessary information.

In yet a further embodiment, the invention is equipped with an USB port and wireless circuit board that will operate and control peripheral devices by the digital interface of the phototherapy device. Peripheral devices are not limited to and include light technology devices and any device that generates frequency or electrical pulse. The peripheral devices will be activated upon a passcode entered into the digital interface of the phototherapy device.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. A phototherapy device for light therapy applications for male genitalia with a shaft with a top and bottom sides, comprising:
- an elongated shaft-containing portion with an interior and an exterior and a distal end and an open proximal end, the interior configured to receive and completely encompass all sides of the shaft of said male genitalia;
- a first plurality of light sources located on the interior of the shaft-containing portion and extending over the majority of the interior, said first plurality of light sources configured to be in direct contact with all sides of the shaft of said male genitalia;

an opening in or proximate to the distal end of the shaft-containing portion;

a cup portion with an exterior and an interior, the cup portion contiguously connected to the shaft-containing portion;

a second plurality of light sources located on the interior of the cup portion;

at least two straps or arms extending contiguously from the cup portion; and a plurality of ventilation holes in at least the cup portion;

wherein the phototherapy device is configured to be worn under clothing; and further wherein each light source of said plurality of light sources comprises a red LED, a green LED, and a blue LED covered in whole or in part by a combination of filler resin and photomixing material.

2. The device of claim 1, wherein the shaft-containing portion comprises a flexible strip.

3. The device of claim 2, wherein the flexible strip forms a helix or spiral encompassing said shaft, with said plurality of light sources in full contact with all sides of the shaft of said male genitalia.

4. The device of claim 1, further comprising a support belt or girdle attached to said cup portion.

5. The device of claim 1, further comprising a control unit in electronic communication with said plurality of light sources.

6. A method of providing light therapy to male genitalia, comprising:

inserting male genitalia with a shaft with a top and bottom sides inside a phototherapy device comprising:

(a) an elongated shaft-containing portion with an interior and an exterior and a distal end and an open proximal end, the interior configured to receive and completely encompass all sides of the shaft, (b) a first plurality of light sources located on the interior of the shaft portion and extending over the majority of the interior, said plurality of first light sources thereby in direct contact with all sides of the shaft of the male genitalia;

(c) an opening in or proximate to the distal end of the shaft-containing portion;

(d) a cup portion with an exterior and an interior, the cup portion contiguously connected to the shaft-containing portion;

(e) a second plurality of light sources located on the interior of the cup portion;

(f) at least two straps or arms extending contiguously from the cup portion; and (g) a plurality of ventilation holes in at least the cup portion;

wherein the phototherapy device is configured to be worn under clothing;

applying various frequencies and intensities of light from said first and second plurality of light sources to said male genitalia;

wherein each light source of said plurality of light sources comprises a red LED, a green LED, and a blue LED covered in whole or in part by a combination of filler resin and photomixing material.

* * * * *